(12) United States Patent
Brun et al.

(10) Patent No.: US 11,221,341 B2
(45) Date of Patent: Jan. 11, 2022

(54) PROCESS FOR IN VITRO DIAGNOSIS OF HEPATIC DISORDERS

(71) Applicants: Commissariat a l'Energie Atomique et aux Energies Alternatives, Paris (FR); Centre Hospitalier Universitaire, La Tronche (FR); Universite Grenoble Alpes, Saint Martin d'Here (FR); INSERM, Paris (FR); Universite Paris Sud, Orsay (FR)

(72) Inventors: Virginie Brun, Seyssins (FR); Jérôme Garin, Corenc (FR); Christophe Bruley, Le Gua (FR); Jamila Faivre, Paris (FR); Jean-Pierre Zarski, St. Nazaire les Eymes (FR); Vincent Leroy, Claix (FR)

(73) Assignees: Commissariat a l'Energie Atomique et aux Energies Alternatives, Paris (FR); Centre Hospitalier Universitaire, La Tronche (FR); Universite Grenoble Alpes, Saint Martin d'Here (FR); Institut National de la Sante et de la Recherche Medicale, Paris (FR); Universite Paris Sud, Orsay (FR)

( * ) Notice: Subject to any disclaimer, the term of this patent is extended or adjusted under 35 U.S.C. 154(b) by 653 days.

(21) Appl. No.: 16/069,362

(22) PCT Filed: Jan. 16, 2017

(86) PCT No.: PCT/FR2017/050089
§ 371 (c)(1),
(2) Date: Jul. 11, 2018

(87) PCT Pub. No.: WO2017/121974
PCT Pub. Date: Jul. 20, 2017

(65) Prior Publication Data
US 2019/0033324 A1    Jan. 31, 2019

(30) Foreign Application Priority Data

Mar. 11, 2016  (FR) ........................... 1652087

(51) Int. Cl.
G01N 33/68     (2006.01)
G01N 33/576    (2006.01)
G01N 30/72     (2006.01)

(52) U.S. Cl.
CPC ....... *G01N 33/6893* (2013.01); *G01N 33/576* (2013.01); *G01N 33/68* (2013.01);
(Continued)

(58) Field of Classification Search
CPC .......... G01N 33/6893; G01N 33/6848; G01N 33/576; G01N 33/68; G01N 2333/91017;
(Continued)

(56) References Cited

U.S. PATENT DOCUMENTS

2015/0147761 A1* 5/2015 Meyer .................. H01J 49/40
435/7.1

FOREIGN PATENT DOCUMENTS

WO    2015/071669 A2    5/2015

OTHER PUBLICATIONS

Janecki et al. (Anal. Biochem., 2007, 369:18-26) (Year: 2007).*
(Continued)

*Primary Examiner* — Jeremy C Flinders
(74) *Attorney, Agent, or Firm* — Morgan, Lewis & Bockius LLP

(57) ABSTRACT

Process for in vitro diagnosis and/or monitoring and/or prognosis and/or theranosis of hepatic disorders from a biological sample originating from a subject, in which process the presence and/or the concentration of the marker ADH1B (SEQ ID NO.2) and/or the presence and/or the (Continued)

concentration of the combination of the markers ADH1B (SEQ ID NO.2) and ADH1A (SEQ ID NO.1) is determined.

21 Claims, 13 Drawing Sheets

Specification includes a Sequence Listing.

(52) U.S. Cl.
CPC .  *G01N 33/6848* (2013.01); *G01N 2333/4742* (2013.01); *G01N 2333/904* (2013.01); *G01N 2333/91005* (2013.01); *G01N 2333/91017* (2013.01); *G01N 2333/91177* (2013.01); *G01N 2333/91188* (2013.01); *G01N 2333/978* (2013.01); *G01N 2800/08* (2013.01); *G01N 2800/085* (2013.01)

(58) Field of Classification Search
CPC ..... G01N 2800/08; G01N 2333/91177; G01N 2333/91188; G01N 2333/4742; G01N 2333/91005; G01N 2800/085; G01N 2333/904; G01N 2333/978
See application file for complete search history.

(56) References Cited

OTHER PUBLICATIONS

Berger et al. (Arch. Toxicol., 2015, 89:1497-1522) (Year: 2015).*
R&D Systems (product manual 2015) (Year: 2015).*
Adrait et al., "Development of a Protein Standard Absolute Quantification (PSAQ) assay for the quantification of *Staphylococcus aureus* enterotoxin A in serum," Journal of Proteomics, 75: 3041-3049 (2012) (abstract only).
Hu et al., "Quantitative Liver-Specific Protein Fingerprint in Blood: A Signature for Hepatotoxicity," Theranostics, 4: 215-228(2014).
Beger et al., "Translational biomarkers of acetaminophen-induced acute liver injury," Arch Toxicol, 89: 1497-1522 (2015).
Ashla et al., "Genetic analysis of expression profile involved in retinoid metabolism in non-alcoholic fatty liver disease," Hepatology Research, 40: 594-604 (2010).
Chaerkady et al., "A Quantitative Proteomic Approach for Identification of Potential Biomarkers in Hepatocellular Carcinoma," Journal of Proteome Research, 7: 4289-4298 (2008).
Lee et al., "Enhanced peptide quantification using spectral count clustering and cluster abundance," BMC Bioinformatics, 12: 423 (2011).
Brun et al., "Isotope dilution strategies for absolute quantitative proteomics," Journal of Proteomics, 72: 740-749 (2009).
International Search Report issued in corresponding International Patent Application No. PCT/FR2017/050089 dated May 4, 2017.
Song et al., "Proteomic analysis on metastasis-associated proteins of human hepatocellular carcinoma tissues," Journal of Cancer Research and Clinical Oncology, 132: 92-98 (2006).

* cited by examiner a)

b)

| Target protein (SEQ ID No.) | Peptide sequence of target proteins wherein the signature peptides of the target proteins are outlined |
|---|---|
| ADH1A (SEQ ID No. 1) | MSTAGKVIKCKAAVLWELKKPFSIEEVEVAPPKAHEVRIKMVAVGICGTDDHVVSGTMVTPLPVILGHEAAGIV ESVGEGVTTVKPGDKVIPLAIPQCGKCRICKNPESNYCLKNDVGNPQGTLQDGTSRFTCRRKPIHHFLGISTF SQYTVVDENAVAKIDAASPLEKVCLIGCGFSTGYGSAVNVAKVTPGSTCAVFGLGGVGLSAIMGCKAAGAAR IIAVGINKDKFAKAKELGATECINPQDYKKPIQEVLKEMTDGGVDFSFEVIGRLDTMMASLLCCHEACGTSVIV GVPPDSQNLSMNPMLLLTGRTWKGAILGGFKSKECVPKLVAQFMAKKFSLDALITHVLPFEKINEGFDLLHS GKSIRTILMF |
| ADH1B (SEQ ID No. 2) | MSTAGKVIKCKAAVLWEVKKPFSIEDVEVAPPKAYEVRIKMVAVGICRTDDHVVSGNLVTPLPVILGHEAAGIV ESVGEGVTTVKPGDKVIPLFTPQCGKCRVCKNPESNYCLKNDLGNPRGTLQDGTSRFTCRGKPIHHFLGTS TFSQYTVVDENAVAKDAASPLEKVCLIGCGFSTGYGSAYNYAKVTPGSTCAVFGLGGVGLSAVMGCKAAG AARIIAVDINKDKFAKAKELGATECNPQDYKKPIQEVLKEMTDGGVDFSFEVIGRLDTMMASLLCCHEACGTS VIVGVPPASQNLSINPMLLLTGRTWKGAVVGGFKSKEGIPKLVADFMAKKFSLDALITHVLPFEKINESFDLL NGGKSIRTVLTF |
| ADH4 – isoform 1 (SEQ ID No. 3) | MGTKGKVIKCKAAIAWEAGKPLCIEEVEVAPPKAHEVRIQMATSLCHTDAYTIDSKFEGLAFPVIVGHEAAGIVE SIGPGVTNVKPGDKVIPLYAPLCRKDKFCLSPLTNLCGKISNLKSPASDQQLMEDKTSRFTCKGKPVYHFFGT STFSQYTVVSDINLAKDDDANLERVCLLGCGFSTGYGAAINNAKVTPGSTCAVFGLGGVGLSAVMGCKAAG ASRSIGDNSEKPVKAKALGATDCLNPRDLHKPQEVIEELTKGGVDFALDCAGSSETMKAALDCTTAGWGSG TFIGVAAGSKGLTIFPEELIGRTINGTPFGGWKSVDSIPKLVTDYKNKKFNLDALVTHTLPFDKISEAFDLMNQ GKSVRTILIF |
| ADH4 – isoform 2 (SEQ ID No. 4) | MLVRGPHPELDRCKTHLFSSNYLTQVIKCKAAIAWEAGKPLCIEEVEVAPPKAHEVRIQMATSLCHTDAYTIDS KFEGLAFPVIVGHEAAGIVESIGPGVTNVKPGDKVIPLYAPLCRKDKFCLSPLTNLCGKISNLKSPASDQQLME DKTSRFTCKGKPVYHFFGTSTFSQYTVVSDINLAKDDDANLERVCLLGCGFSTGYGAAINNAKVTPGSTCAV FGLGGVGLSAVMGCKAAGASRSIGDNSEKPVKAKALGATDCLNPRDLHKPQEVIEELTKGGVDFALDCAGS SETMKAALDCTTAGWGSCTFIGVAAGSKGLTIFPEELIGRTINGTPFGGWKSVDSIPKLVTDYKNKKFNLDAL VTHTLPFDKISEAFDLMNQGKSVRTILIF |
| BHMT1 (SEQ ID No. 5) | MPPYGGSKAPKIGILERLNAGEIVIGDGGFVFALEKRGYVKAGPWTPEAAVEHPEAVRQLHREFLRAGSNVM QTFTFYASEDKLENRGNYVLEKICSGQEVNEAACDIAROVAGDEGDALVAGQVSQTPSYLSCKSETEVKKVFLQ QLEVFMRKNVDFLIAEYFEHVEEAVWAVETLIASGKPVAATMCIGPEGDLHGVPPGECAVRLVKAGASIIGVR CHFDPTISLKTVKLMIKEGLEAARLKAHLMSQPLAYHTPDCNKCGFDLPEFPFGLEPRVATRWDIQKYAREA YNLGVRYIGGCCGFEPYHINAIAEELAPERGFLPPASEKHGSWVGSGLDMHTKPWVRARARKEYWENLRIAS GRPYNPSMSKPDCWGVTKGTAELMQQKEATTEQGLKELFEKQKFKSQ |
| BHMT2 - isoform 1 (SEQ ID No. 6) | MAPAGRPGAKKGILERLESGEVVIGDGSFLITLEKRGYVKAGLWTPEAVIEHPDAVRQLHMEFLRAGSNVMQ TFTFSASEDNMESKWEDVNAAACDLARSVAGKGDALVAGGICQTSIYKYQKDEARKKLFRQQLEVFAWKN VDFLIAEYFEHVEEAVWAVEVLKESDRPVAVTMCIGPECGDMHDITPGECAVRLVKAGASIVQVNCRFGPOTS LKTMELMIKEGLEWAGLKAHLMVQPLGFHAPDCQKEGPVDLPEYPFGLESRVATRWDIQKYAREAYNLGVR YIGGCCGFEPYHIRAIAEELAPERGFLPPASEKHGSWGSGLDMHTKPWIRARARREYWENLLPASGRPFCP SLSKPDF |
| BHMT2 - isoform 2 (SEQ ID No. 7) | MAPAGRPGAKKGILERLESGEVVIGDGSFLITLEKRGYVKAGLWTPEAVIEHPDAVRQLHMEFLRAGSNVMQ TFTFSASEDNMESKYFEHVEEAVWAVEVLKESDRPVAVTMCIGPECGDMHDITPGECAVRLVKAGASIVQVN CRFGPOTSLKTMELMKEGLEWAGLKAHLMVQPLGFHAPDCQKEGFVDLPEYPFGLESRVATRWDIQKYAR EAYNLGVRYIGGCCGFEPYHIRAIAEELAPERGFLPRASEKHGSWGSGLDMHTKPWIRARARREYWENLLP ASGRPFCPSLSKPDF |
| ARG1 – isoform 1 (SEQ ID No. 8) | MSAKSRTIGIIGAPFSKGQPRGGVEEGPTVLRKAGLLEKLKEQECDVKDYSDLPFADIPNDSPFQIVKNPRSV GKASEQLAGKVAEVKKNGRISLVLGGDHSLAIGSISGHARVHPDLGVIWVDAHTDINTPLTTTSGNLHGQPVS FLLKELKGKIPDVPGFSWVTPCISAKDIVYIGLRDVDPGEHYILKTLGIKYFSMTEVDRLGIGKVMEETSYLLG RKKRPIHLSFDVDGLDPSFTPATGTPVVGGLTYREGLYITEEIYKTGLLSGLDIMEVNPSLGKTPEEVTRTVNT AVAITLACFGLAREGNHKPIDYLNPPK |
| ARG1 – isoform 2 (SEQ ID No. 9) | MSAKSRTIGIIGAPFSKGQPRGGVEEGPTVLRKAGLLEKLKEQVTQNFLLLECCDVKDYGDLPFADIPNDSPFQI VKNPRSVGKASEQLAGKVAEVKKNGRISLVLGGDHSLAIGSISGHARVHPDLGVIWVDAHTDINTPLTTTSGN LHGQPVSFLLKELKGKIPDVPGFSWVTPCISAKDIVYIGLRDVDPGEHYILKTLGIKYFSMTEVDRLGIGKVME ETLSYLLGRKKRPIHLSFDVDGLDPSFTPATGTPVVGGLTYREGLYITEEIYKTGLLSGLDIMEVNPSLGKTPE EVTRTVNTAVAITLACFGLAREGNHKPIDYLNPPK |
| ARG1 – isoform 3 (SEQ ID No. 10) | MSAKSRTIGIIGAPFSKGQPRGGVEEGPTVLRKAGLLEKLKEQECDVKDYSDLPFADIPNDSPFQIVKNPRSV GKASEQLAGKVAEVKKNGRISLVLGGDHSLAIGSISGHARVHPDLGVIWVDAHTDINTPLTTTSGNLHGQPVS FLLKELKGKIPDVPGFSWVTPCISAKDIVYIGLRDVDPGEHYILKTLGIKYFSMTEVTRTVNTAVAITLACFGLA REGNHKPIDYLNPPK |
| FABP1 (SEQ ID No. 11) | MSFSGKYQLQSQENFEAFMKAIGLPEELIQKGKDIKGVSEIVQNGKHFKFTITAGSKVIQNEFTVGEECELET MTGEKVKTVVQLEGDNKLVTTFKNIKSVTELNGDIITNTMTLGDIVFKRISKRI |
| GSTA1 (SEQ ID No. 12) | MAEKPKLHYFNARGRMESTRWLLAAAGVEFEEKFIKSAEDLDKLRNDGYLMFQQVPMVEIDGMKLVQTRAI LNYIASKYNLYGKDIKERALIDMYIEGIADLGEMILLLPVCPPEEKDAKLALIKEKIKNRYFPAFEKVLKSHGQDY LVGNKLSRADIHLVELLYYVEELDSSLISSFPLLKALKTRISNLPTVEKFLQPGSPRKPPMDEKSLEEARKIFRF |
| ALT1 (SEQ ID No. 13) | MASSTGDAVRHGLRAKVLTLDGMNPRVRRVEYAVRGPIVQRALELEGELRGQVKSPFTEVYRANGDA QAMGQRPITFLRQVLALCVNPDLLSSPNFPDDAKKRAEIRLDACGGHSLGAYSVSSGIQLIREDVARYIERRD GGIPADPNNVFLSTGASDAIVTVLKLVAGEGHTRTGVLIPIPQYPRLYSATLAELGAVQVDYYLDEERAWALD VAELHRALGQARDHCRPRALCVINPGNPTGQVQTRECIEAVIRFAFEERLFLLADEVYQDNVYAAGSQFHSF KKVLMGMGPPYAGQQELASFHGTSKGYMGECGFRGNYVEVVNMDAAVQQQMLKLMSVRLCPPVPGQALL QLVVSPFAPTDFSFAQFQAEKQAVLAELAAKARLTEQVFNEAPGISCNPVQGAMYSFPRVQLPPRAVERACG ELGLAPDMFECLRLLEETGICVVPGSGFGQREGTYHFRMTILPPLEKLRLLLEKLSRFHAKFTLEYS |

Figure 8

SEQUENCE LISTING

<160> NUMBER OF SEQ ID NOS: 36

<210> SEQ ID NO 1
<211> LENGTH: 375

<212> TYPE: PRT
<213> ORGANISM: Homo sapiens

<400> SEQUENCE: 1

Met Ser Thr Ala Gly Lys Val Ile Lys Cys Lys Ala Ala Val Leu Trp
1               5                   10                  15

Glu Leu Lys Lys Pro Phe Ser Ile Glu Val Glu Val Ala Pro Pro
            20                  25                  30

Lys Ala His Glu Val Arg Ile Lys Met Val Ala Val Gly Ile Cys Gly
            35                  40                  45

Thr Asp Asp His Val Val Ser Gly Thr Met Val Thr Pro Leu Pro Val
    50                  55                  60

Ile Leu Gly His Glu Ala Ala Gly Ile Val Glu Ser Val Gly Glu Gly
65                  70                  75                  80

Val Thr Thr Val Lys Pro Gly Asp Lys Val Ile Pro Leu Ala Ile Pro
                85                  90                  95

Gln Cys Gly Lys Cys Arg Ile Cys Lys Asn Pro Glu Ser Asn Tyr Cys
            100                 105                 110

Leu Lys Asn Asp Val Ser Asn Pro Gln Gly Thr Leu Gln Asp Gly Thr
            115                 120                 125

Ser Arg Phe Thr Cys Arg Arg Lys Pro Ile His His Phe Leu Gly Ile
130                 135                 140

Ser Thr Phe Ser Gln Tyr Thr Val Val Asp Glu Asn Ala Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Asn Val Ala Lys Val Thr Pro
            180                 185                 190

Gly Ser Thr Cys Ala Val Phe Gly Leu Gly Gly Val Gly Leu Ser Ala
            195                 200                 205

Ile Met Gly Cys Lys Ala Ala Gly Ala Ala Arg Ile Ile Ala Val Asp
            210                 215                 220

Ile Asn Lys Asp Lys Phe Ala Lys Ala Lys Glu Leu Gly Ala Thr Glu
225                 230                 235                 240

Cys Ile Asn Pro Gln Asp Tyr Lys Lys Pro Ile Gln Glu Val Leu Lys
                245                 250                 255

Glu Met Thr Asp Gly Gly Val Asp Phe Ser Phe Glu Val Ile Gly Arg
            260                 265                 270

Leu Asp Thr Met Met Ala Ser Leu Leu Cys Cys His Glu Ala Cys Gly
            275                 280                 285

Thr Ser Val Ile Val Gly Val Pro Pro Asp Ser Gln Asn Leu Ser Met
290                 295                 300

Asn Pro Met Leu Leu Leu Thr Gly Arg Thr Trp Lys Gly Ala Ile Leu
305                 310                 315                 320

Gly Gly Phe Lys Ser Lys Glu Cys Val Pro Lys Leu Val Ala Asp Phe
                325                 330                 335

Met Ala Lys Lys Phe Ser Leu Asp Ala Leu Ile Thr His Val Leu Pro
            340                 345                 350

Phe Glu Lys Ile Asn Glu Gly Phe Asp Leu Leu His Ser Gly Lys Ser
            355                 360                 365

Ile Arg Thr Ile Leu Met Phe
370                 375

<210> SEQ ID NO 2

```
<211> LENGTH: 375
<212> TYPE: PRT
<213> ORGANISM: Homo sapiens

<400> SEQUENCE: 2

Met Ser Thr Ala Gly Lys Val Ile Lys Cys Lys Ala Ala Val Leu Trp
1               5                   10                  15

Glu Val Lys Lys Pro Phe Ser Ile Glu Asp Val Glu Val Ala Pro Pro
            20                  25                  30

Lys Ala Tyr Glu Val Arg Ile Lys Met Val Ala Val Gly Ile Cys Arg
        35                  40                  45

Thr Asp Asp His Val Val Ser Gly Asn Leu Val Thr Pro Leu Pro Val
50                  55                  60

Ile Leu Gly His Glu Ala Ala Gly Ile Val Glu Ser Val Gly Glu Gly
65                  70                  75                  80

Val Thr Thr Val Lys Pro Gly Asp Lys Val Ile Pro Leu Phe Thr Pro
                85                  90                  95

Gln Cys Gly Lys Cys Arg Val Cys Lys Asn Pro Glu Ser Asn Tyr Cys
            100                 105                 110

Leu Lys Asn Asp Leu Gly Asn Pro Arg Gly Thr Leu Gln Asp Gly Thr
        115                 120                 125

Arg Arg Phe Thr Cys Arg Gly Lys Pro Ile His His Phe Leu Gly Thr
    130                 135                 140

Ser Thr Phe Ser Gln Tyr Thr Val Val Asp Glu Asn Ala Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Asn Val Ala Lys Val Thr Pro
            180                 185                 190

Gly Ser Thr Cys Ala Val Phe Gly Leu Gly Gly Val Gly Leu Ser Ala
        195                 200                 205

Val Met Gly Cys Lys Ala Ala Gly Ala Ala Arg Ile Ile Ala Val Asp
    210                 215                 220

Ile Asn Lys Asp Lys Phe Ala Lys Ala Lys Glu Leu Gly Ala Thr Glu
225                 230                 235                 240

Cys Ile Asn Pro Gln Asp Tyr Lys Lys Pro Ile Gln Glu Val Leu Lys
                245                 250                 255

Glu Met Thr Asp Gly Gly Val Asp Phe Ser Phe Glu Val Ile Gly Arg
            260                 265                 270

Leu Asp Thr Met Met Ala Ser Leu Leu Cys Cys His Glu Ala Cys Gly
        275                 280                 285

Thr Ser Val Ile Val Gly Val Pro Pro Ala Ser Gln Asn Leu Ser Ile
    290                 295                 300

Asn Pro Met Leu Leu Leu Thr Gly Arg Thr Trp Lys Gly Ala Val Tyr
305                 310                 315                 320

Gly Gly Phe Lys Ser Lys Glu Gly Ile Pro Lys Leu Val Ala Asp Phe
                325                 330                 335

Met Ala Lys Lys Phe Ser Leu Asp Ala Leu Ile Thr His Val Leu Pro
            340                 345                 350

Phe Glu Lys Ile Asn Glu Gly Phe Asp Leu Leu His Ser Gly Lys Ser
        355                 360                 365

Ile Arg Thr Val Leu Thr Phe
    370                 375
```

```
<210> SEQ ID NO 3
<211> LENGTH: 380
<212> TYPE: PRT
<213> ORGANISM: Homo sapiens

<400> SEQUENCE: 3

Met Gly Thr Lys Gly Lys Val Ile Lys Cys Lys Ala Ala Ile Ala Trp
1               5                   10                  15

Glu Ala Gly Lys Pro Leu Cys Ile Glu Glu Val Glu Val Ala Pro Pro
            20                  25                  30

Lys Ala His Glu Val Arg Ile Gln Ile Ile Ala Thr Ser Leu Cys His
        35                  40                  45

Thr Asp Ala Thr Val Ile Asp Ser Lys Phe Glu Gly Leu Ala Phe Pro
50                  55                  60

Val Ile Val Gly His Glu Ala Ala Gly Ile Val Glu Ser Ile Gly Pro
65                  70                  75                  80

Gly Val Thr Asn Val Lys Pro Gly Asp Lys Val Ile Pro Leu Tyr Ala
                85                  90                  95

Pro Leu Cys Arg Lys Cys Lys Phe Cys Leu Ser Pro Leu Thr Asn Leu
            100                 105                 110

Cys Gly Lys Ile Ser Asn Leu Lys Ser Pro Ala Ser Asp Gln Gln Leu
        115                 120                 125

Met Glu Asp Lys Thr Ser Arg Phe Thr Cys Lys Gly Lys Pro Val Tyr
130                 135                 140

His Phe Phe Gly Thr Ser Thr Phe Ser Gln Tyr Thr Val Val Ser Asp
145                 150                 155                 160

Ile Asn Leu Ala Lys Ile Asp Asp Ala Asn Leu Glu Arg Val Cys
                165                 170                 175

Leu Leu Gly Cys Gly Phe Ser Thr Gly Tyr Gly Ala Ala Ile Asn Asn
            180                 185                 190

Ala Lys Val Thr Pro Gly Ser Thr Cys Ala Val Phe Gly Leu Gly Gly
        195                 200                 205

Val Gly Leu Ser Ala Val Met Gly Cys Lys Ala Ala Gly Ala Ser Arg
210                 215                 220

Ile Ile Gly Ile Asp Ile Asn Ser Glu Lys Phe Val Lys Ala Lys Ala
225                 230                 235                 240

Leu Gly Ala Thr Asp Cys Leu Asn Pro Arg Asp Leu His Lys Pro Ile
            245                 250                 255

Gln Glu Val Ile Ile Glu Leu Thr Lys Gly Gly Val Asp Phe Ala Leu
        260                 265                 270

Asp Cys Ala Gly Gly Ser Glu Thr Met Lys Ala Ala Leu Asp Cys Thr
275                 280                 285

Thr Ala Gly Trp Gly Ser Cys Thr Phe Ile Gly Val Ala Ala Gly Ser
290                 295                 300

Lys Gly Leu Thr Ile Phe Pro Glu Glu Leu Ile Ile Gly Arg Thr Ile
305                 310                 315                 320

Asn Gly Thr Phe Phe Gly Gly Trp Lys Ser Val Asp Ser Ile Pro Lys
            325                 330                 335

Leu Val Thr Asp Tyr Lys Asn Lys Phe Asn Leu Asp Ala Leu Val
        340                 345                 350

Thr His Thr Leu Pro Phe Asp Lys Ile Ser Glu Ala Phe Asp Leu Met
355                 360                 365

Asn Gln Gly Lys Ser Val Arg Thr Ile Leu Ile Phe
370                 375                 380
```

<210> SEQ ID NO 4
<211> LENGTH: 399
<212> TYPE: PRT
<213> ORGANISM: Homo sapiens

<400> SEQUENCE: 4

Met Leu Val Arg Gly Pro His Phe Glu Leu Gln Arg Cys Lys Thr His
1               5                   10                  15

Leu Phe Ser Ser Asn Tyr Leu Thr Gln Val Ile Lys Cys Lys Ala Ala
            20                  25                  30

Ile Ala Trp Glu Ala Gly Lys Pro Leu Cys Ile Glu Glu Val Glu Val
        35                  40                  45

Ala Pro Pro Lys Ala His Glu Val Arg Ile Gln Ile Ile Ala Thr Ser
    50                  55                  60

Leu Cys His Thr Asp Ala Thr Val Ile Asp Ser Lys Phe Glu Gly Leu
65                  70                  75                  80

Ala Phe Pro Val Ile Val Gly His Glu Ala Ala Gly Ile Val Glu Ser
                85                  90                  95

Ile Gly Pro Gly Val Thr Asn Val Lys Pro Gly Asp Lys Val Ile Pro
            100                 105                 110

Leu Tyr Ala Pro Leu Cys Arg Lys Cys Lys Phe Cys Leu Ser Pro Leu
        115                 120                 125

Thr Asn Leu Cys Gly Lys Ile Ser Asn Leu Lys Ser Pro Ala Ser Asp
    130                 135                 140

Gln Gln Leu Met Glu Asp Lys Thr Ser Arg Phe Thr Cys Lys Gly Lys
145                 150                 155                 160

Pro Val Tyr His Phe Phe Gly Thr Ser Thr Phe Ser Gln Tyr Thr Val
                165                 170                 175

Val Ser Asp Ile Asn Leu Ala Lys Ile Asp Asp Ala Asn Leu Glu
            180                 185                 190

Arg Val Cys Leu Leu Gly Cys Gly Phe Ser Thr Gly Tyr Gly Ala Ala
        195                 200                 205

Ile Asn Asn Ala Lys Val Thr Pro Gly Ser Thr Cys Ala Val Phe Gly
    210                 215                 220

Leu Gly Gly Val Gly Leu Ser Ala Val Met Gly Cys Lys Ala Ala Gly
225                 230                 235                 240

Ala Ser Arg Ile Ile Gly Ile Asp Ile Asn Ser Glu Lys Phe Val Lys
                245                 250                 255

Ala Lys Ala Leu Gly Ala Thr Asp Cys Leu Asn Pro Arg Asp Leu His
            260                 265                 270

Lys Pro Ile Gln Glu Val Ile Glu Leu Thr Lys Gly Gly Val Asp
        275                 280                 285

Phe Ala Leu Asp Cys Ala Gly Gly Ser Glu Thr Met Lys Ala Ala Leu
    290                 295                 300

Asp Cys Thr Thr Ala Gly Trp Gly Ser Cys Thr Phe Ile Gly Val Ala
305                 310                 315                 320

Ala Gly Ser Lys Gly Leu Thr Ile Phe Pro Glu Leu Ile Ile Gly
                325                 330                 335

Arg Thr Ile Asn Gly Thr Phe Phe Gly Gly Trp Lys Ser Val Asp Ser
            340                 345                 350

Ile Pro Lys Leu Val Thr Asp Tyr Lys Asn Lys Lys Phe Asn Leu Asp
        355                 360                 365

Ala Leu Val Thr His Thr Leu Pro Phe Asp Lys Ile Ser Glu Ala Phe
    370                 375                 380

Asp Leu Met Asn Gln Gly Lys Ser Val Arg Thr Ile Leu Ile Phe
385                 390                 395

<210> SEQ ID NO 5
<211> LENGTH: 406
<212> TYPE: PRT
<213> ORGANISM: Homo sapiens

<400> SEQUENCE: 5

Met Pro Pro Val Gly Gly Lys Lys Ala Lys Gly Ile Leu Glu Arg
1               5                   10                  15

Leu Asn Ala Gly Glu Ile Val Ile Gly Asp Gly Gly Phe Val Phe Ala
            20                  25                  30

Leu Glu Lys Arg Gly Tyr Val Lys Ala Gly Pro Trp Thr Pro Glu Ala
            35                  40                  45

Ala Val Glu His Pro Glu Ala Val Arg Gln Leu His Arg Glu Phe Leu
            50                  55                  60

Arg Ala Gly Ser Asn Val Met Gln Thr Phe Thr Phe Tyr Ala Ser Glu
65                  70                  75                  80

Asp Lys Leu Glu Asn Arg Gly Asn Tyr Val Leu Glu Lys Ile Ser Gly
                85                  90                  95

Gln Glu Val Asn Glu Ala Ala Cys Asp Ile Ala Arg Gln Val Ala Asp
            100                 105                 110

Glu Gly Asp Ala Leu Val Ala Gly Val Ser Gln Thr Pro Ser Tyr
            115                 120                 125

Leu Ser Cys Lys Ser Glu Thr Glu Val Lys Lys Val Phe Leu Gln Gln
130                 135                 140

Leu Glu Val Phe Met Lys Lys Asn Val Asp Phe Leu Ile Ala Glu Tyr
145                 150                 155                 160

Phe Glu His Val Glu Glu Ala Val Trp Ala Val Glu Thr Leu Ile Ala
            165                 170                 175

Ser Gly Lys Pro Val Ala Ala Thr Met Cys Ile Gly Pro Glu Gly Asp
            180                 185                 190

Leu His Gly Val Pro Pro Gly Glu Cys Ala Val Arg Leu Val Lys Ala
            195                 200                 205

Gly Ala Ser Ile Ile Gly Val Asn Cys His Phe Asp Pro Thr Ile Ser
210                 215                 220

Leu Lys Thr Val Lys Leu Met Lys Glu Gly Leu Glu Ala Ala Arg Leu
225                 230                 235                 240

Lys Ala His Leu Met Ser Gln Pro Leu Ala Tyr His Thr Pro Asp Cys
            245                 250                 255

Asn Lys Gln Gly Phe Ile Asp Leu Pro Glu Phe Pro Phe Gly Leu Glu
            260                 265                 270

Pro Arg Val Ala Thr Arg Trp Asp Ile Gln Lys Tyr Ala Arg Glu Ala
            275                 280                 285

Tyr Asn Leu Gly Val Arg Tyr Ile Gly Gly Cys Cys Gly Phe Glu Pro
            290                 295                 300

Tyr His Ile Arg Ala Ile Ala Glu Glu Leu Ala Pro Glu Arg Gly Phe
305                 310                 315                 320

Leu Pro Pro Ala Ser Glu Lys His Gly Ser Trp Gly Ser Gly Leu Asp
            325                 330                 335

Met His Thr Lys Pro Trp Val Arg Ala Arg Ala Arg Lys Glu Tyr Trp
            340                 345                 350

Glu Asn Leu Arg Ile Ala Ser Gly Arg Pro Tyr Asn Pro Ser Met Ser

```
                355                 360                 365
Lys Pro Asp Gly Trp Gly Val Thr Lys Gly Thr Ala Glu Leu Met Gln
    370                 375                 380
Gln Lys Glu Ala Thr Thr Glu Gln Gln Leu Lys Glu Leu Phe Glu Lys
385                 390                 395                 400
Gln Lys Phe Lys Ser Gln
            405

<210> SEQ ID NO 6
<211> LENGTH: 363
<212> TYPE: PRT
<213> ORGANISM: Homo sapiens

<400> SEQUENCE: 6

Met Ala Pro Ala Gly Arg Pro Ala Lys Lys Gly Ile Leu Glu Arg
1               5                   10                  15

Leu Glu Ser Gly Glu Val Val Ile Gly Asp Gly Ser Phe Leu Ile Thr
                20                  25                  30

Leu Glu Lys Arg Gly Tyr Val Lys Ala Gly Leu Trp Thr Pro Glu Ala
            35                  40                  45

Val Ile Glu His Pro Asp Ala Val Arg Gln Leu His Met Glu Phe Leu
        50                  55                  60

Arg Ala Gly Ser Asn Val Met Gln Thr Phe Thr Phe Ser Ala Ser Glu
65                  70                  75                  80

Asp Asn Met Glu Ser Lys Trp Glu Asp Val Asn Ala Ala Cys Asp
                85                  90                  95

Leu Ala Arg Glu Val Ala Gly Lys Gly Asp Ala Leu Val Ala Gly Gly
            100                 105                 110

Ile Cys Gln Thr Ser Ile Tyr Lys Tyr Gln Lys Asp Glu Ala Arg Ile
        115                 120                 125

Lys Lys Leu Phe Arg Gln Gln Leu Glu Val Phe Ala Trp Lys Asn Val
    130                 135                 140

Asp Phe Leu Ile Ala Glu Tyr Phe Glu His Val Glu Glu Ala Val Trp
145                 150                 155                 160

Ala Val Glu Val Leu Lys Glu Ser Asp Arg Pro Val Ala Val Thr Met
                165                 170                 175

Cys Ile Gly Pro Glu Gly Asp Met His Asp Ile Thr Pro Gly Glu Cys
            180                 185                 190

Ala Val Arg Leu Val Lys Ala Gly Ala Ser Ile Val Gly Val Asn Cys
        195                 200                 205

Arg Phe Gly Pro Asp Thr Ser Leu Lys Thr Met Glu Leu Met Lys Glu
    210                 215                 220

Gly Leu Glu Trp Ala Gly Leu Lys Ala His Leu Met Val Gln Pro Leu
225                 230                 235                 240

Gly Phe His Ala Pro Asp Cys Gly Lys Glu Gly Phe Val Asp Leu Pro
                245                 250                 255

Glu Tyr Pro Phe Gly Leu Glu Ser Arg Val Ala Thr Arg Trp Asp Ile
            260                 265                 270

Gln Lys Tyr Ala Arg Glu Ala Tyr Asn Leu Gly Val Arg Tyr Ile Gly
        275                 280                 285

Gly Cys Cys Gly Phe Glu Pro Tyr His Ile Arg Ala Ile Ala Glu Glu
    290                 295                 300

Leu Ala Pro Glu Arg Gly Phe Leu Pro Pro Ala Ser Glu Lys His Gly
305                 310                 315                 320
```

```
Ser Trp Gly Ser Gly Leu Asp Met His Thr Lys Pro Trp Ile Arg Ala
            325                 330                 335

Arg Ala Arg Arg Glu Tyr Trp Glu Asn Leu Leu Pro Ala Ser Gly Arg
            340                 345                 350

Pro Phe Cys Pro Ser Leu Ser Lys Pro Asp Phe
            355                 360

<210> SEQ ID NO 7
<211> LENGTH: 299
<212> TYPE: PRT
<213> ORGANISM: Homo sapiens

<400> SEQUENCE: 7

Met Ala Pro Ala Gly Arg Pro Gly Ala Lys Lys Gly Ile Leu Glu Arg
1               5                   10                  15

Leu Glu Ser Gly Glu Val Val Ile Gly Asp Gly Ser Phe Leu Ile Thr
            20                  25                  30

Leu Glu Lys Arg Gly Tyr Val Lys Ala Gly Leu Trp Thr Pro Glu Ala
        35                  40                  45

Val Ile Glu His Pro Asp Ala Val Arg Gln Leu His Met Glu Phe Leu
    50                  55                  60

Arg Ala Gly Ser Asn Val Met Gln Thr Phe Thr Phe Ser Ala Ser Glu
65                  70                  75                  80

Asp Asn Met Glu Ser Lys Tyr Phe Glu His Val Glu Glu Ala Val Trp
                85                  90                  95

Ala Val Glu Val Leu Lys Glu Ser Asp Arg Pro Val Ala Val Thr Met
            100                 105                 110

Cys Ile Gly Pro Glu Gly Asp Met His Asp Ile Thr Pro Gly Glu Cys
        115                 120                 125

Ala Val Arg Leu Val Lys Ala Gly Ala Ser Ile Val Gly Val Asn Cys
    130                 135                 140

Arg Phe Gly Pro Asp Thr Ser Leu Lys Thr Met Glu Leu Met Lys Glu
145                 150                 155                 160

Gly Leu Glu Trp Ala Gly Leu Lys Ala His Leu Met Val Gln Pro Leu
                165                 170                 175

Gly Phe His Ala Pro Asp Cys Gly Lys Glu Gly Phe Val Asp Leu Pro
            180                 185                 190

Glu Tyr Pro Phe Gly Leu Glu Ser Arg Val Ala Thr Arg Trp Asp Ile
        195                 200                 205

Gln Lys Tyr Ala Arg Glu Ala Tyr Asn Leu Gly Val Arg Tyr Ile Gly
    210                 215                 220

Gly Cys Cys Gly Phe Glu Pro Tyr His Ile Arg Ala Ile Ala Glu Glu
225                 230                 235                 240

Leu Ala Pro Glu Arg Gly Phe Leu Pro Pro Ala Ser Glu Lys His Gly
                245                 250                 255

Ser Trp Gly Ser Gly Leu Asp Met His Thr Lys Pro Trp Ile Arg Ala
            260                 265                 270

Arg Ala Arg Arg Glu Tyr Trp Glu Asn Leu Leu Pro Ala Ser Gly Arg
        275                 280                 285

Pro Phe Cys Pro Ser Leu Ser Lys Pro Asp Phe
    290                 295

<210> SEQ ID NO 8
<211> LENGTH: 322
<212> TYPE: PRT
<213> ORGANISM: Homo sapiens
```

<400> SEQUENCE: 8

```
Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys
```

<210> SEQ ID NO 9
<211> LENGTH: 330
<212> TYPE: PRT
<213> ORGANISM: Homo sapiens

<400> SEQUENCE: 9

```
Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30
```

```
Lys Ala Gly Leu Leu Glu Lys Leu Lys Glu Gln Val Thr Gln Asn Phe
            35                  40                  45

Leu Ile Leu Glu Cys Asp Val Lys Asp Tyr Gly Asp Leu Pro Phe Ala
 50                  55                  60

Asp Ile Pro Asn Asp Ser Pro Phe Gln Ile Val Lys Asn Pro Arg Ser
 65                  70                  75                  80

Val Gly Lys Ala Ser Glu Gln Leu Ala Gly Lys Val Ala Glu Val Lys
                 85                  90                  95

Lys Asn Gly Arg Ile Ser Leu Val Leu Gly Gly Asp His Ser Leu Ala
            100                 105                 110

Ile Gly Ser Ile Ser Gly His Ala Arg Val His Pro Asp Leu Gly Val
            115                 120                 125

Ile Trp Val Asp Ala His Thr Asp Ile Asn Thr Pro Leu Thr Thr Thr
130                 135                 140

Ser Gly Asn Leu His Gly Gln Pro Val Ser Phe Leu Leu Lys Glu Leu
145                 150                 155                 160

Lys Gly Lys Ile Pro Asp Val Pro Gly Phe Ser Trp Val Thr Pro Cys
                165                 170                 175

Ile Ser Ala Lys Asp Ile Val Tyr Ile Gly Leu Arg Asp Val Asp Pro
            180                 185                 190

Gly Glu His Tyr Ile Leu Lys Thr Leu Gly Ile Lys Tyr Phe Ser Met
            195                 200                 205

Thr Glu Val Asp Arg Leu Gly Ile Gly Lys Val Met Glu Glu Thr Leu
210                 215                 220

Ser Tyr Leu Leu Gly Arg Lys Arg Pro Ile His Leu Ser Phe Asp
225                 230                 235                 240

Val Asp Gly Leu Asp Pro Ser Phe Thr Pro Ala Thr Gly Thr Pro Val
                245                 250                 255

Val Gly Gly Leu Thr Tyr Arg Glu Gly Leu Tyr Ile Thr Glu Glu Ile
            260                 265                 270

Tyr Lys Thr Gly Leu Leu Ser Gly Leu Asp Ile Met Glu Val Asn Pro
            275                 280                 285

Ser Leu Gly Lys Thr Pro Glu Glu Val Thr Arg Thr Val Asn Thr Ala
290                 295                 300

Val Ala Ile Thr Leu Ala Cys Phe Gly Leu Ala Arg Glu Gly Asn His
305                 310                 315                 320

Lys Pro Ile Asp Tyr Leu Asn Pro Pro Lys
                325                 330

<210> SEQ ID NO 10
<211> LENGTH: 236
<212> TYPE: PRT
<213> ORGANISM: Homo sapiens

<400> SEQUENCE: 10

Met Ser Ala Lys Ser Arg Thr Ile Gly Ile Ile Gly Ala Pro Phe Ser
 1               5                  10                  15

Lys Gly Gln Pro Arg Gly Gly Val Glu Glu Gly Pro Thr Val Leu Arg
                 20                  25                  30

Lys Ala Gly Leu Leu Glu Lys Leu Lys Glu Gln Glu Cys Asp Val Lys
            35                  40                  45

Asp Tyr Gly Asp Leu Pro Phe Ala Asp Ile Pro Asn Asp Ser Pro Phe
 50                  55                  60

Gln Ile Val Lys Asn Pro Arg Ser Val Gly Lys Ala Ser Glu Gln Leu
 65                  70                  75                  80
```

Ala Gly Lys Val Ala Glu Val Lys Lys Asn Gly Arg Ile Ser Leu Val
            85                  90                  95

Leu Gly Gly Asp His Ser Leu Ala Ile Gly Ser Ile Ser Gly His Ala
        100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Thr Arg Thr Val Asn
        195                 200                 205

Thr Ala Val Ala Ile Thr Leu Ala Cys Phe Gly Leu Ala Arg Glu Gly
    210                 215                 220

Asn His Lys Pro Ile Asp Tyr Leu Asn Pro Pro Lys
225                 230                 235

<210> SEQ ID NO 11
<211> LENGTH: 127
<212> TYPE: PRT
<213> ORGANISM: Homo sapiens

<400> SEQUENCE: 11

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125

<210> SEQ ID NO 12
<211> LENGTH: 222
<212> TYPE: PRT
<213> ORGANISM: Homo sapiens

<400> SEQUENCE: 12

Met Ala Glu Lys Pro Lys Leu His Tyr Phe Asn Ala Arg Gly Arg Met
1               5                   10                  15

Glu Ser Thr Arg Trp Leu Leu Ala Ala Ala Gly Val Glu Phe Glu Glu
            20                  25                  30

Lys Phe Ile Lys Ser Ala Glu Asp Leu Asp Lys Leu Arg Asn Asp Gly
        35                  40                  45

Tyr Leu Met Phe Gln Gln Val Pro Met Val Glu Ile Asp Gly Met Lys
    50                  55                  60

Leu Val Gln Thr Arg Ala Ile Leu Asn Tyr Ile Ala Ser Lys Tyr Asn
65                  70                  75                  80

Leu Tyr Gly Lys Asp Ile Lys Glu Arg Ala Leu Ile Asp Met Tyr Ile
                    85                  90                  95

Glu Gly Ile Ala Asp Leu Gly Glu Met Ile Leu Leu Pro Val Cys
                100                 105                 110

Pro Pro Glu Glu Lys Asp Ala Lys Leu Ala Leu Ile Lys Glu Lys Ile
                115                 120                 125

Lys Asn Arg Tyr Phe Pro Ala Phe Glu Lys Val Leu Lys Ser His Gly
130                 135                 140

Gln Asp Tyr Leu Val Gly Asn Lys Leu Ser Arg Ala Asp Ile His Leu
145                 150                 155                 160

Val Glu Leu Leu Tyr Tyr Val Glu Glu Leu Asp Ser Ser Leu Ile Ser
                    165                 170                 175

Ser Phe Pro Leu Leu Lys Ala Leu Lys Thr Arg Ile Ser Asn Leu Pro
                180                 185                 190

Thr Val Lys Lys Phe Leu Gln Pro Gly Ser Pro Arg Lys Pro Pro Met
                195                 200                 205

Asp Glu Lys Ser Leu Glu Glu Ala Arg Lys Ile Phe Arg Phe
210                 215                 220

<210> SEQ ID NO 13
<211> LENGTH: 496
<212> TYPE: PRT
<213> ORGANISM: Homo sapiens

<400> SEQUENCE: 13

Met Ala Ser Ser Thr Gly Asp Arg Ser Gln Ala Val Arg His Gly Leu
1               5                   10                  15

Arg Ala Lys Val Leu Thr Leu Asp Gly Met Asn Pro Arg Val Arg Arg
                20                  25                  30

Val Glu Tyr Ala Val Arg Gly Pro Ile Val Gln Arg Ala Leu Glu Leu
                35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Leu Arg Gln Val Leu Ala Leu Cys Val Asn Pro Asp Leu Leu Ser
                85                  90                  95

Ser Pro Asn Phe Pro Asp Asp Ala Lys Lys Arg Ala Glu Arg Ile Leu
                100                 105                 110

Gln Ala Cys Gly Gly His Ser Leu Gly Ala Tyr Ser Val Ser Ser Gly
                115                 120                 125

Ile Gln Leu Ile Arg Glu Asp Val Ala Arg Tyr Ile Glu Arg Arg Asp
                130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                    165                 170                 175

His Thr Arg Thr Gly Val Leu Ile Pro Ile Pro Gln Tyr Pro Leu Tyr
                180                 185                 190

Ser Ala Thr Leu Ala Glu Leu Gly Ala Val Gln Val Asp Tyr Tyr Leu

```
            195                 200                 205
Asp Glu Glu Arg Ala Trp Ala Leu Asp Val Ala Glu Leu His Arg Ala
    210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
            275                 280                 285

Phe Lys Lys Val Leu Met Glu Met Gly Pro Pro Tyr Ala Gly Gln Gln
            290                 295                 300

Glu Leu Ala Ser Phe His Ser Thr Ser Lys Gly Tyr Met Gly Glu Cys
305                 310                 315                 320

Gly Phe Arg Gly Gly Tyr Val Glu Val Val Asn Met Asp Ala Ala Val
                325                 330                 335

Gln Gln Gln Met Leu Lys Leu Met Ser Val Arg Leu Cys Pro Pro Val
            340                 345                 350

Pro Gly Gln Ala Leu Leu Asp Leu Val Val Ser Pro Pro Ala Pro Thr
            355                 360                 365

Asp Pro Ser Phe Ala Gln Phe Gln Ala Glu Lys Gln Ala Val Leu Ala
            370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
                405                 410                 415

Arg Val Gln Leu Pro Pro Arg Ala Val Glu Arg Ala Gln Glu Leu Gly
            420                 425                 430

Leu Ala Pro Asp Met Phe Phe Cys Leu Arg Leu Leu Glu Glu Thr Gly
            435                 440                 445

Ile Cys Val Val Pro Gly Ser Gly Phe Gly Gln Arg Glu Gly Thr Tyr
            450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
                485                 490                 495

<210> SEQ ID NO 14
<211> LENGTH: 9
<212> TYPE: PRT
<213> ORGANISM: Homo sapiens

<400> SEQUENCE: 14

Ile Asp Ala Ala Ser Pro Leu Glu Lys
1               5

<210> SEQ ID NO 15
<211> LENGTH: 15
<212> TYPE: PRT
<213> ORGANISM: Homo sapiens

<400> SEQUENCE: 15

Phe Ser Leu Asp Ala Leu Ile Thr His Val Leu Pro Phe Glu Lys
1               5                   10                  15
```

```
<210> SEQ ID NO 16
<211> LENGTH: 12
<212> TYPE: PRT
<213> ORGANISM: Homo sapiens

<400> SEQUENCE: 16

Ile Asn Glu Gly Phe Asp Leu Leu His Ser Gly Lys
1               5                   10

<210> SEQ ID NO 17
<211> LENGTH: 8
<212> TYPE: PRT
<213> ORGANISM: Homo sapiens

<400> SEQUENCE: 17

Ala Ala Val Leu Trp Glu Val Lys
1               5

<210> SEQ ID NO 18
<211> LENGTH: 9
<212> TYPE: PRT
<213> ORGANISM: Homo sapiens

<400> SEQUENCE: 18

Ile Asp Asp Asp Ala Asn Leu Glu Arg
1               5

<210> SEQ ID NO 19
<211> LENGTH: 10
<212> TYPE: PRT
<213> ORGANISM: Homo sapiens

<400> SEQUENCE: 19

Ile Ile Gly Ile Asp Ile Asn Ser Glu Lys
1               5                   10

<210> SEQ ID NO 20
<211> LENGTH: 15
<212> TYPE: PRT
<213> ORGANISM: Homo sapiens

<400> SEQUENCE: 20

Phe Asn Leu Asp Ala Leu Val Thr His Thr Leu Pro Phe Asp Lys
1               5                   10                  15

<210> SEQ ID NO 21
<211> LENGTH: 9
<212> TYPE: PRT
<213> ORGANISM: Homo sapiens

<400> SEQUENCE: 21

Glu Ala Thr Thr Glu Gln Gln Leu Lys
1               5

<210> SEQ ID NO 22
<211> LENGTH: 8
<212> TYPE: PRT
<213> ORGANISM: Homo sapiens

<400> SEQUENCE: 22

Glu Ala Tyr Asn Leu Gly Val Arg
1               5

<210> SEQ ID NO 23
<211> LENGTH: 10
```

```
<212> TYPE: PRT
<213> ORGANISM: Homo sapiens

<400> SEQUENCE: 23

Ala Ile Ala Glu Glu Leu Ala Pro Glu Arg
1               5                   10

<210> SEQ ID NO 24
<211> LENGTH: 11
<212> TYPE: PRT
<213> ORGANISM: Homo sapiens

<400> SEQUENCE: 24

Thr Ile Gly Ile Ile Gly Ala Pro Phe Ser Lys
1               5                   10

<210> SEQ ID NO 25
<211> LENGTH: 11
<212> TYPE: PRT
<213> ORGANISM: Homo sapiens

<400> SEQUENCE: 25

Asp Val Asp Pro Gly Glu His Tyr Ile Leu Lys
1               5                   10

<210> SEQ ID NO 26
<211> LENGTH: 11
<212> TYPE: PRT
<213> ORGANISM: Homo sapiens

<400> SEQUENCE: 26

Glu Gly Leu Tyr Ile Thr Glu Glu Ile Tyr Lys
1               5                   10

<210> SEQ ID NO 27
<211> LENGTH: 11
<212> TYPE: PRT
<213> ORGANISM: Homo sapiens

<400> SEQUENCE: 27

Ala Ile Gly Leu Pro Glu Glu Leu Ile Gln Lys
1               5                   10

<210> SEQ ID NO 28
<211> LENGTH: 8
<212> TYPE: PRT
<213> ORGANISM: Homo sapiens

<400> SEQUENCE: 28

Phe Thr Ile Thr Ala Gly Ser Lys
1               5

<210> SEQ ID NO 29
<211> LENGTH: 10
<212> TYPE: PRT
<213> ORGANISM: Homo sapiens

<400> SEQUENCE: 29

Thr Val Val Gln Leu Glu Gly Asp Asn Lys
1               5                   10

<210> SEQ ID NO 30
<211> LENGTH: 7
<212> TYPE: PRT
<213> ORGANISM: Homo sapiens
```

<400> SEQUENCE: 30

Leu His Tyr Phe Asn Ala Arg
1               5

<210> SEQ ID NO 31
<211> LENGTH: 11
<212> TYPE: PRT
<213> ORGANISM: Homo sapiens

<400> SEQUENCE: 31

Ser His Gly Gln Asp Tyr Leu Val Gly Asn Lys
1               5                   10

<210> SEQ ID NO 32
<211> LENGTH: 9
<212> TYPE: PRT
<213> ORGANISM: Homo sapiens

<400> SEQUENCE: 32

Ala Ile Leu Asn Tyr Ile Ala Ser Lys
1               5

<210> SEQ ID NO 33
<211> LENGTH: 8
<212> TYPE: PRT
<213> ORGANISM: Homo sapiens

<400> SEQUENCE: 33

Ile Ser Asn Leu Pro Thr Val Lys
1               5

<210> SEQ ID NO 34
<211> LENGTH: 9
<212> TYPE: PRT
<213> ORGANISM: Homo sapiens

<400> SEQUENCE: 34

Ala Leu Glu Leu Glu Gln Glu Leu Arg
1               5

<210> SEQ ID NO 35
<211> LENGTH: 10
<212> TYPE: PRT
<213> ORGANISM: Homo sapiens

<400> SEQUENCE: 35

Leu Leu Val Ala Gly Glu Gly His Thr Arg
1               5                   10

<210> SEQ ID NO 36
<211> LENGTH: 8
<212> TYPE: PRT
<213> ORGANISM: Homo sapiens

<400> SEQUENCE: 36

Lys Pro Phe Thr Glu Val Ile Arg
1               5

PROCESS FOR IN VITRO DIAGNOSIS OF HEPATIC DISORDERS

SEQUENCE LISTING SUBMISSION VIA EFS-WEB

A computer readable text file, entitled "SequenceListing.txt" created on or about Jul. 10, 2018 with a file size of about 41 kb contains the sequence listing for this application and is hereby incorporated by reference in its entirety.

FIELD OF THE INVENTION

The invention belongs to the field of hepatology (medicine of the liver) and relates to the use of biomarkers for diagnosing liver disorders. More specifically, this invention relates to methods for in vitro diagnosis and/or monitoring and/or in vitro prognosis of hepatic disorders such as acute liver injury and failure or steatohepatitis by the detection and/or assay of certain biomarkers.

STATE OF THE RELATED ART

Hepatic disorders include a multitude of diseases affecting the liver chronically (such as cirrhosis) or acutely (this is referred to as acute liver injury). The causes thereof are varied and include alcoholism, hepatitis A, B, C and E viruses, genetic disorders (Wilson's disease) or immune disorders (autoimmune hepatitis), drug poisoning or excess fat associated with obesity.

Acute Liver Injury (abbreviated herein as ALI) or Acute Liver Failure (abbreviated herein as ALF) occur suddenly in patients with no pre-existing liver disease. The causes thereof are varied: medicinal products (including paracetamol), viruses, autoimmune disease. Acute liver injuries are characterised by the death of liver cells (hepatocytes) in a necrotic and/or apoptotic mode and result in a reduction in functional liver mass. These hepatic disorders are associated with blood clotting disorders and modification in clinico-biological investigation parameters of the liver (increase in transaminase and serum CK18). In the most severe form thereof (fulminant hepatitis or ALF), encephalopathy is also present. Acute liver disorders may result in the patient's death without suitable medical care.

Non-Alcoholic Fatty Liver Diseases (known as the acronym NAFLD) are very frequent liver diseases. They encompass a wide range of diseases such as isolated steatosis (known as the acronym NAFL—"Non-Alcoholic Fatty Liver"), non-alcoholic steatohepatitis (NASH) and cirrhosis. They are associated with an abnormal accumulation of fat in the liver. They are linked with increase in the prevalence of diabetes and obesity. Non-alcoholic steatohepatitis (NASH) is a potentially serious disease which can progress to cirrhosis and induce chronic or acute liver injury and/or hepatocellular carcinoma.

Hepatic disorders may be diagnosed by the detection or assay in the blood of certain specific molecules (biomarkers). Cytolysis (hepatocyte necrosis) is assessed by the detection of proteins, contained in liver cells, and which are discharged into the bloodstream following liver cell necrosis (mechanistic biomarkers): this is the case of transaminases which reflect liver cell lysis. However, transaminases are not specific to the liver and the blood concentrations thereof may increase following disorders in other organs (heart, muscle). These may also consist of molecules synthesised by the liver, the function whereof is impacted by the decrease in the synthesis thereof (functional biomarkers): this is the case of the prothrombin index which investigates the clotting factors I, II, V, VII and X synthesised by the liver. However, due to the half-life in the blood of a few hours of clotting factors, clotting disorders are not immediate.

With respect to non-alcoholic and alcoholic hepatic steatosis, formal diagnosis is usually carried out on a liver biopsy from the patient; as such, it is possible to assess the liver tissue lesions and determine the severity of the disease. A biopsy is an invasive test, associated with bleeding risks, and requires hospital care; therefore, it is a costly test. It would be preferable to be able to detect liver disorders and monitor the progression thereof using non-invasive methods, preferably using a biological fluid, for example obtained from a mere blood sample.

In recent years, a number of non-invasive methods for assessing liver lesions have been proposed, particularly for detecting alcoholic and non-alcoholic steatohepatitis. By way of example, US 2006/0 172 286 describes a non-invasive process for diagnosing non-alcoholic or alcoholic steatohepatitis in a patient, comprising the measurement of the three biochemical markers ApoAI, ALT and AST in a serum or plasma sample. WO 2010/058 295 describes a process for quantifying a patient's liver lesions via the assay of one or a plurality of biomarkers (of which ALT). Zhiyuan Hu et al. (Theranostics, 2014, 4, 215-228) and Beger et al. (Arch. Toxicol., 2015, 89, 1497-1552) describe biomarkers of acute liver lesions induced by paracetamol including the conventional marker transaminase (ALT1), as well as other markers such as BHMT, particularly BHMT1. WO 2015/071 669 describes a method for the diagnosis, prognosis or monitoring of a liver tumour in a subject via the detection or quantification or one or a plurality of markers present in particular in the blood; the list of markers is extremely large and particularly comprises the proteins ADH1A, ADH1B, GSTA1, FABP1, ARG1, GPT1 (corresponding to ALT1), BHMT and ADH4.

In any case, absolute quantification, i.e. the determination of the concentration of proteins or peptides present in a liquid sample, particularly a blood sample may be a relatively complex process.

It is observed that diagnosing hepatic disorders at an early stage and predicting the progression of these disorders has become a major health challenge, in particular for non-alcoholic steatohepatitis, the prevalence whereof increases with obesity.

The present invention seeks to propose a process for in vitro diagnosis of hepatic disorders, more particularly a novel non-invasive diagnostic test of hepatic disorders more accurate than the diagnosis processes according to the prior art.

Subject Matter of the Invention

The present invention relates to a process for in vitro diagnosis and/or monitoring and/or prognosis and/or theranostics of hepatic disorders from a biological sample originating from a subject, in which process the presence and/or concentration of the marker ADH1B (SEQ ID NO. 2) and/or the presence and/or concentration of the combination of the markers ADH1B (SEQ ID NO. 2) and ADH1A (SEQ ID NO. 1) is determined.

The invention also relates to the use of at least one marker ADH1B (SEQ ID NO. 2) and/or of at least the combination of the markers ADH1B (SEQ ID NO. 2) and ADH1A (SEQ ID NO. 1) for in vitro diagnosis, monitoring, prognosis and/or theranostics of hepatic disorders from a biological sample originating from a subject; in which use the presence and/or concentration of said marker is determined.

In one embodiment of the process or of the use above, the presence and/or concentration of at least one additional marker, preferentially of at least two additional markers, and even more preferentially of at least three additional markers is determined, said markers being selected in the group consisting of: ADH4 (SEQ ID NO. 3 & SEQ ID NO. 4), BHMT (SEQ ID NO. 5, SEQ ID NO. 6 & SEQ ID NO. 7), ARG1 (SEQ ID NO. 8, SEQ ID NO. 9 & SEQ ID NO. 10), FABP1 (SEQ ID NO. 11), GSTA1 (SEQ ID NO. 12) and ALT1 (SEQ ID NO. 13).

In one embodiment of the process or of the use above, at least the presence and/or concentration of at least one additional marker selected among ADH4 (SEQ ID NO. 3 & SEQ ID NO. 4) and BHMT (SEQ ID NO. 5, SEQ ID NO. 6 & SEQ ID NO. 7) is determined.

In one embodiment of the process or of the use above, at least the presence and/or concentration of the marker ADH1B (SEQ ID NO. 2) or of the combination of the markers ADH1B (SEQ ID NO. 2) and ADH1A (SEQ ID NO. 1), on one hand, and of the markers ADH4 (SEQ ID NO. 3 & SEQ ID NO. 4) and BHMT (SEQ ID NO. 5, SEQ ID NO. 6 & SEQ ID NO. 7), on the other, is determined.

In one advantageous embodiment of the process or of the use above, the marker BHMT is the sequence variant BHMT1 (SEQ ID NO. 5) and/or the combination of the sequence variants BHMT1 (SEQ ID NO. 5) and BHMT2 (SEQ ID NO. 6 & SEQ ID NO. 7).

In one embodiment of the process or of the use described above, the presence and/or concentration of the marker CK18 is further determined.

In one embodiment of the process or of the use described above, signature peptides present in said markers are used for said determination of the presence and/or concentration of said markers.

In one advantageous embodiment of the process or of the use described above, said signature peptides are generated from said markers by a digestion process, preferably enzymatic.

In one embodiment of the process or of the use described above, the presence and/or concentration:

a. of the combination of the markers ADH1A (SEQ ID NO. 1) and ADH1B (SEQ ID NO. 2), if it is selected, is determined by the presence of at least one signature peptide chosen among INEGFDLLHSK (SEQ ID NO. 16) and FSLDALITHVLPFEK (SEQ ID NO. 15), b. of the marker ADH1B (SEQ ID NO. 2), if it is selected, is determined by the presence of the signature peptide AAVLWEVK (SEQ ID NO. 17), c. of the marker ADH4 (SEQ ID NO. 3 & SEQ ID NO. 4), if it is selected, is determined by the presence of at least one signature peptide chosen among FNLDALVTHTLPFDK (SEQ ID NO. 20), IDDDANLER (SEQ ID NO. 18) or IIGIDINSEK (SEQ ID NO. 19), d. of the marker ARG1 (SEQ ID NO. 8, SEQ ID NO. 9 & SEQ ID NO. 10), if it is selected, is determined by the presence of at least one signature peptide chosen among DVDPGEHYILK (SEQ ID NO. 25), TIGIIGAPFSK (SEQ ID NO. 24) or EGLYITEEIYK (SEQ ID NO. 26), e. of the marker BHMT (SEQ ID NO. 5, SEQ ID NO. 6 & SEQ ID NO. 7), if it is selected, is determined by the presence of at least one signature peptide chosen among EATTEQQLK (SEQ ID NO. 21), AIAEELAPER (SEQ ID NO. 23) or EAYNLGVR (SEQ ID NO. 22), f. of the marker BHMT1 (SEQ ID NO. 5), if it is selected, is determined by the presence of the signature peptide EATTEQQLK (SEQ ID NO. 21), g. of the combination of the markers BHMT1 (SEQ ID NO. 5) and BHMT2 (SEQ ID NO. 6 & SEQ ID NO. 7), if it is selected, is determined by the presence of at least one signature peptide chosen among AIAEELAPER (SEQ ID NO. 23) or EAYNLGVR (SEQ ID NO. 22), h. of the marker FABP1 (SEQ ID NO. 11), if it is selected, is determined by the presence of at least one signature peptide chosen among AIGLPEELIQK (SEQ ID NO. 27), FTITAGSK (SEQ ID NO. 28) or TVVQLEGDNK (SEQ ID NO. 29), i. of the marker GSTA1 (SEQ ID NO. 12), if it is selected, is determined by the presence of the signature peptide LHYFNAR (SEQ ID NO. 30), j. of the marker ALT1 (SEQ ID NO. 13), if it is selected, is determined by the presence of at least one signature peptide chosen among ALELEQELR (SEQ ID NO. 34), LLVAGEGHTR (SEQ ID NO. 35) or KPFTEVIR (SEQ ID NO. 36), in the knowledge that ALT1 (SEQ ID NO. 13), if it is selected, is more particularly determined by the presence of the signature peptide ALELEQELR (SEQ ID NO. 34) or LLVAGEGHTR (SEQ ID NO. 35).

In one advantageous embodiment of the process of use described above, the process of use, wherein at least one of said markers (referred to as "selected marker"), of which at least one marker ADH1B (SEQ ID NO. 2) and/or the combination of the markers ADH1B (SEQ ID NO. 2) and ADH1A (SEQ ID NO. 1), is assayed by means of at least one signature peptide characteristic of said marker, comprises the following steps:

a) obtaining a biological sample taken from a subject at the time $t_0$, b) adding a known quantity of an isotopically labelled homologous protein (referred to as "standard") of the selected marker in the biological sample obtained in step a), c) treating the sample to extract at least a portion of the abundant proteins or at least a portion of the glycoproteins, d) treating the sample after extracting at least a portion of the abundant proteins or glycoproteins to generate proteolytic peptides, preferably by digestion, it being understood that the proteolytic proteins obtained include the signature peptides of the selected markers, e) quantitative assay by mass spectrometry of at least one signature peptide generated from the selected marker, f) determining a ratio of the abundance of the isotopically labelled signature peptide, from the standard, added in step b), to the abundance of the non-labelled signature peptide from the biological sample, g) computing based on the ratio obtained in step f) and on the known quantity of said isotopically labelled protein added in step b), the concentration of said selected marker in the sample.

In one advantageous embodiment, step c) of the process or of the use described above is performed by depletion and preferentially by glycodepletion.

In one advantageous embodiment, step c) of the process or of the use described above is followed by a biological sample electrophoresis step.

In one advantageous embodiment, the process is performed at a time $t_0$ and at a time $t_1$ greater than $t_0$, and comprises after step g) the comparison of the concentration of the selected marker in the sample between $t_1$ and $t_0$.

In one advantageous embodiment, step d) of the process described above is performed by enzymatic digestion, preferably by using trypsin or a mixture of EndolysC and trypsin.

In one advantageous embodiment, the liver disorder is acute liver injury, liver steatosis or steatohepatitis, preferably, acute liver injury or steatohepatitis. The acute hepatitis is particularly viral hepatitis, alcoholic hepatitis, drug-induced hepatitis, poisoning-related hepatitis, for example due to fungi or vitamins, autoimmune hepatitis or Wilson's disease; preferably, it consists of non-alcoholic hepatitis, such as in particular drug-induced hepatitis, for example due to paracetamol or another medicinal product. The liver steatosis is in particular non-alcoholic steatosis, such as isolated steatosis (NAFL for "Non-Alcoholic Fatty Liver"). The steatohepatitis is in particular non-alcoholic steatohepatitis (NASH for "Non-Alcoholic SteatoHepatitis"). Further subject matter of the invention relates to a use of the process for assessing the toxicity of molecules (candidate medicinal products, medicinal products, xenobiotic) previously administered to the subject from whom said biological sample originates.

DESCRIPTION OF THE FIGURES

FIGS. 1 to 8 illustrate certain aspects of the invention.

FIG. 1 describes the principle of plasma protein glycodepletion for the assay of non-glycosylated biomarkers (such as hepatocytic lysis proteins).

The plasma proteome is composed (by weight) of 50% glycosylated proteins and 50% non-glycosylated proteins. The glycosylated proteins may be captured on magnetic beads functionalised with hydrazide via covalent bond formation. The non-glycosylated proteins are subsequently eluted with urea suitable for breaking the protein/protein interactions.

Figure 2:
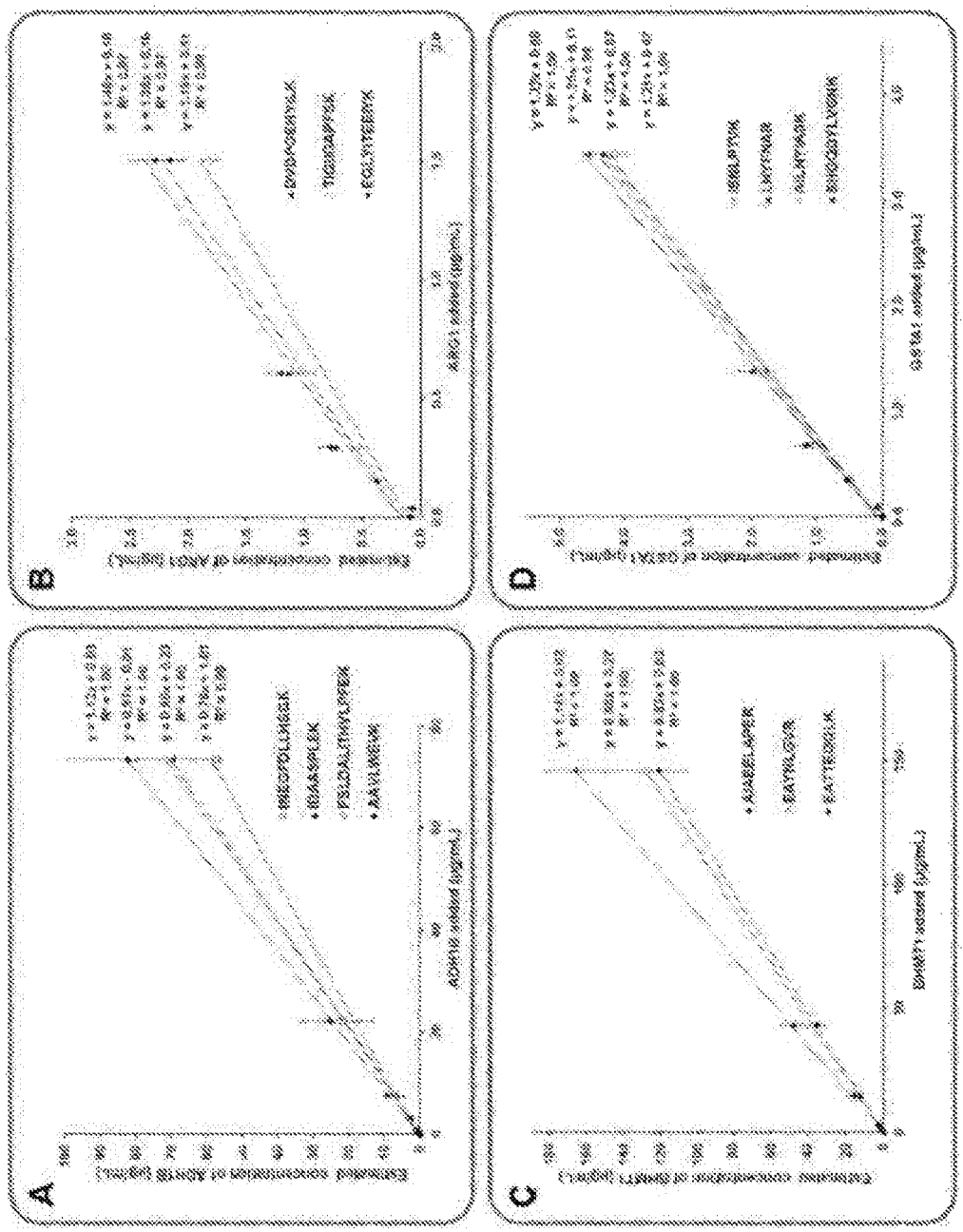

FIG. 2 shows the calibration curves obtained for ADH1B, ARG1, BHMT1 and GSTA1 in plasma after immunodepletion. These calibration curves are suitable for assessing the analytical performances of the assay method.

Figure 3:
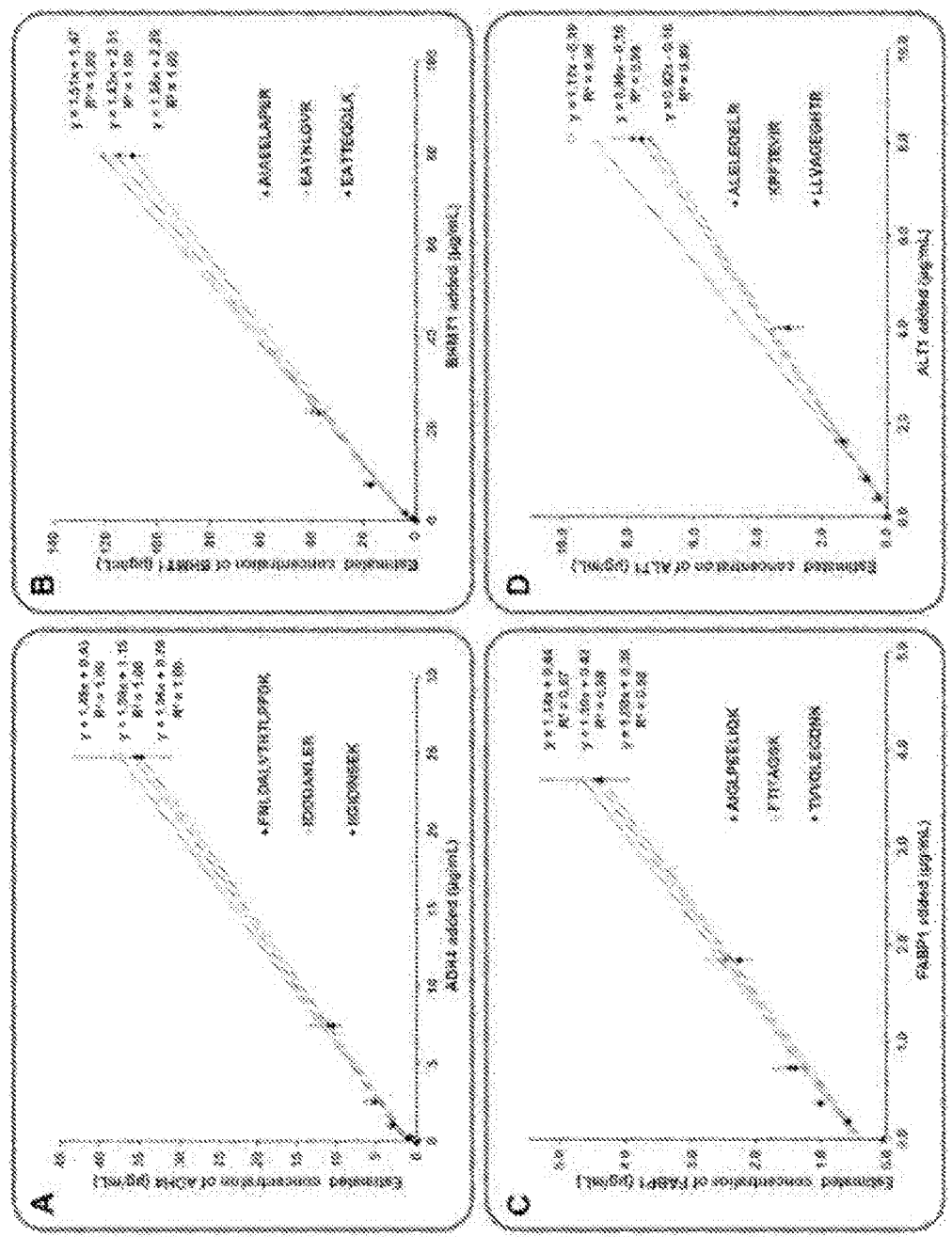
Figure 4A:
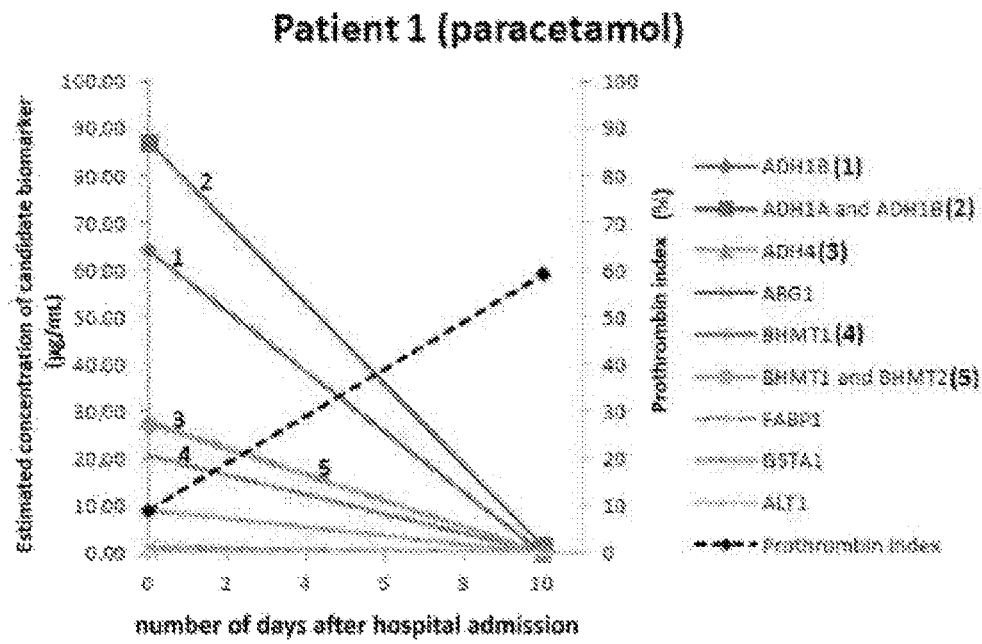
Figure 4B:
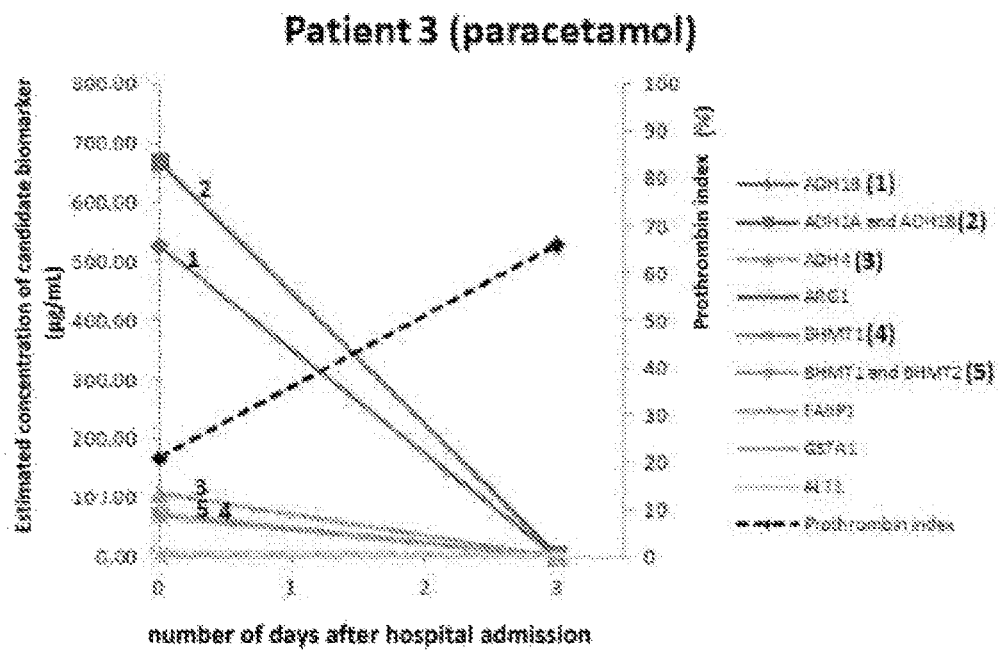
Figure 4C:
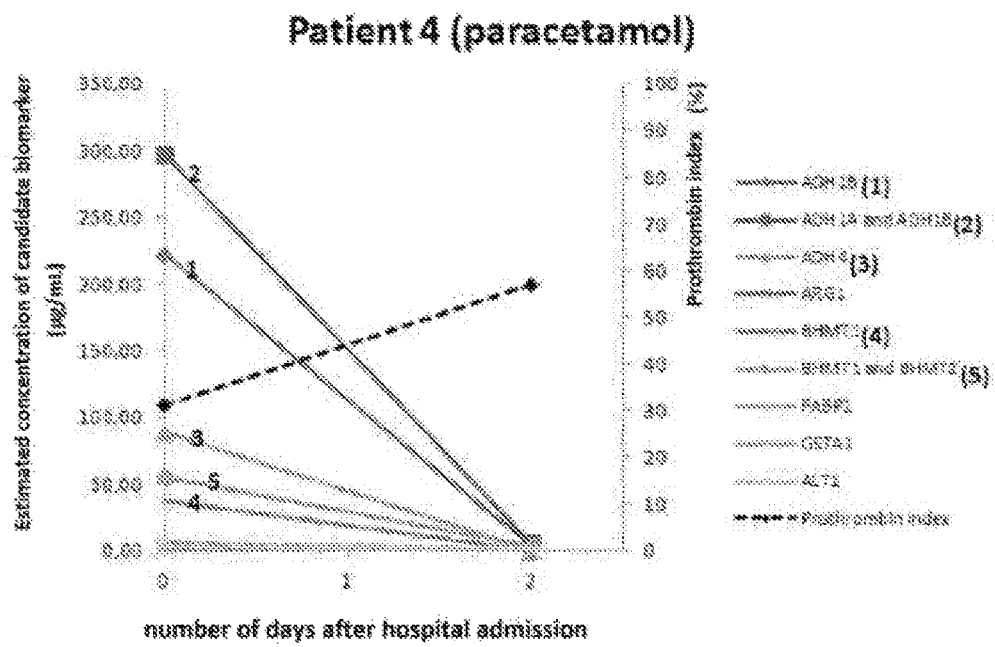
Figure 4D:
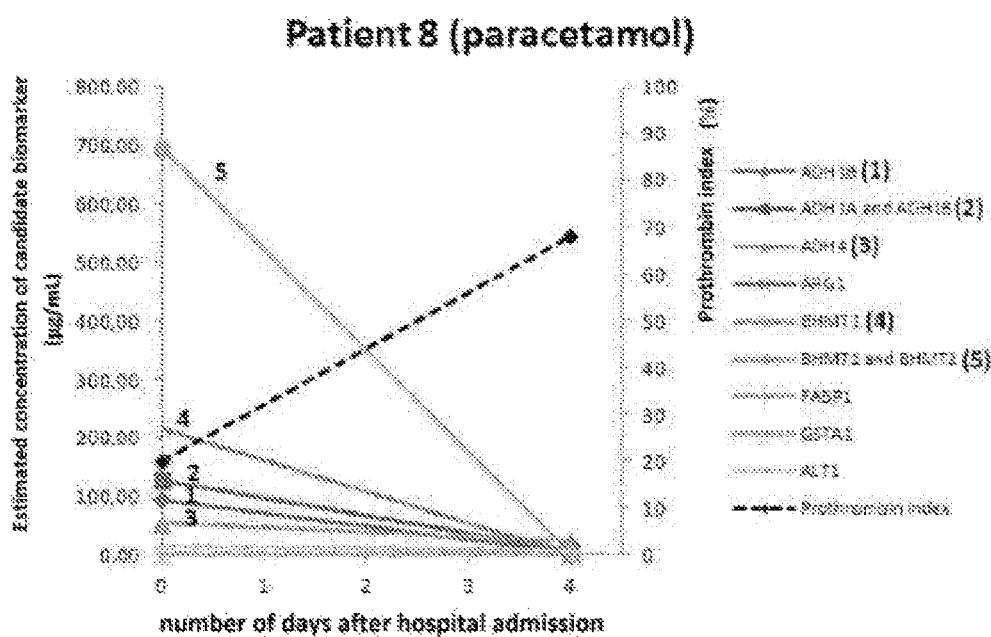
Figure 4E:
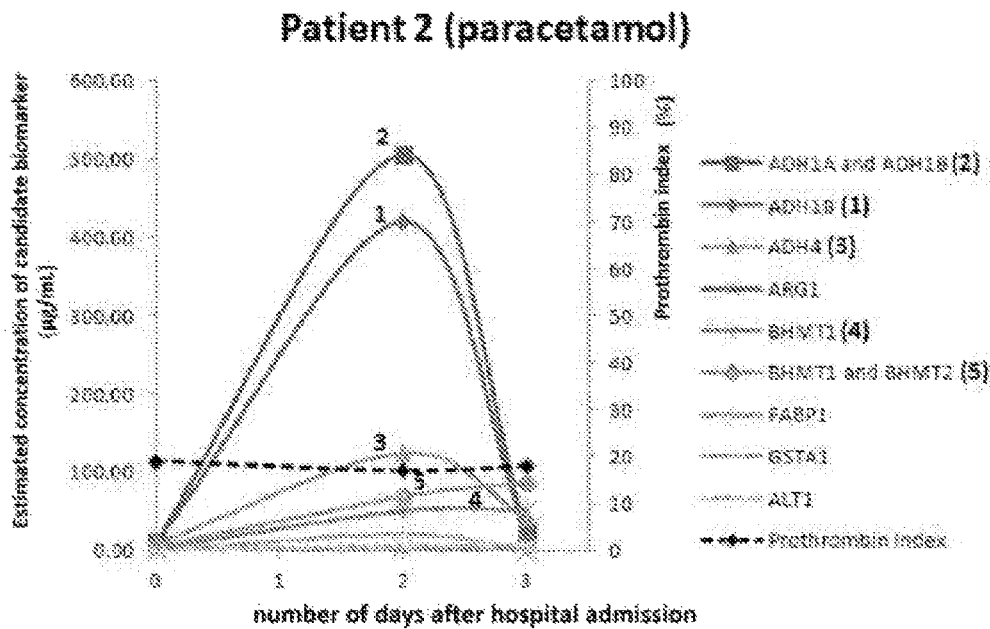
Figure 4F:
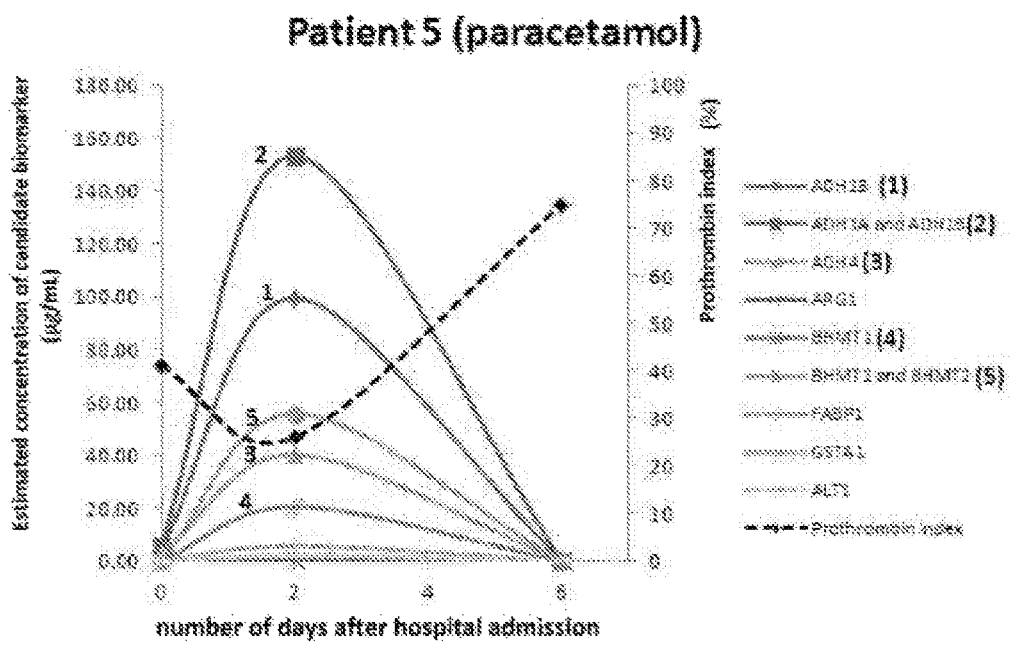
Figure 4G:
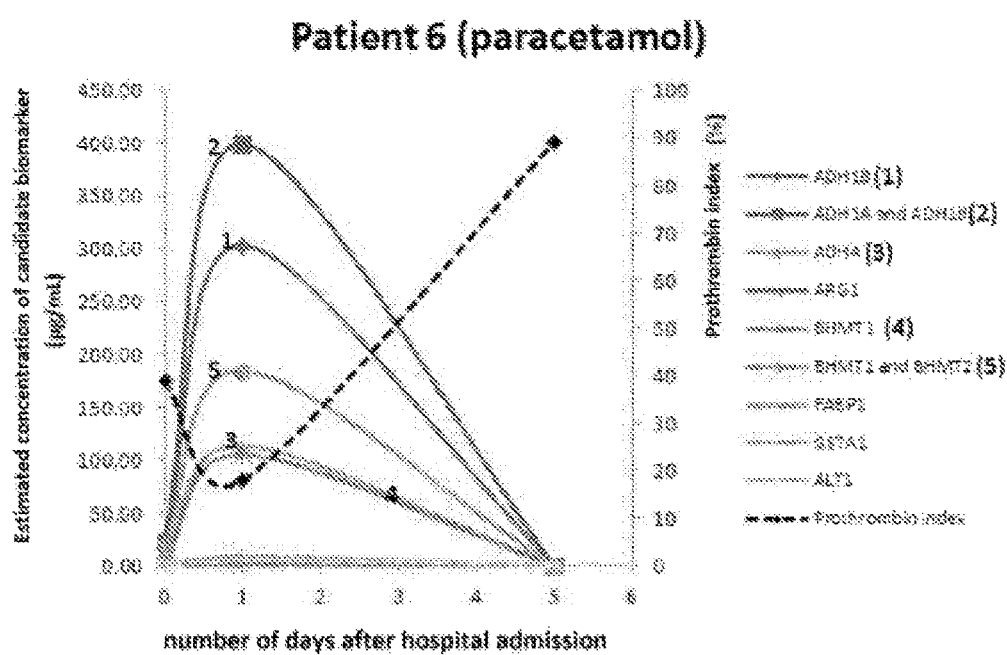
Figure 5A:
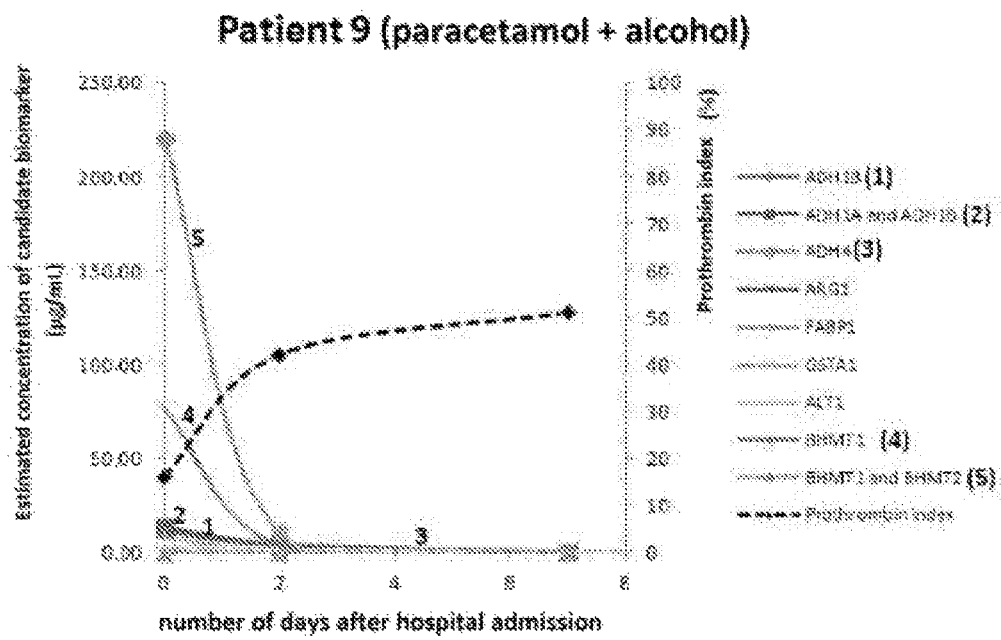
Figure 5B:
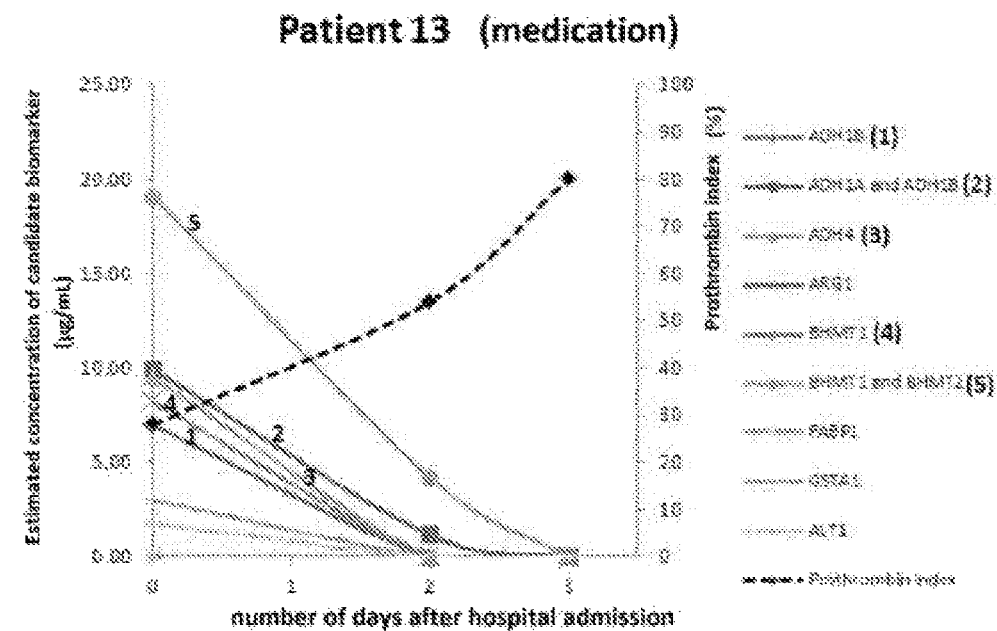
Figure 5C:
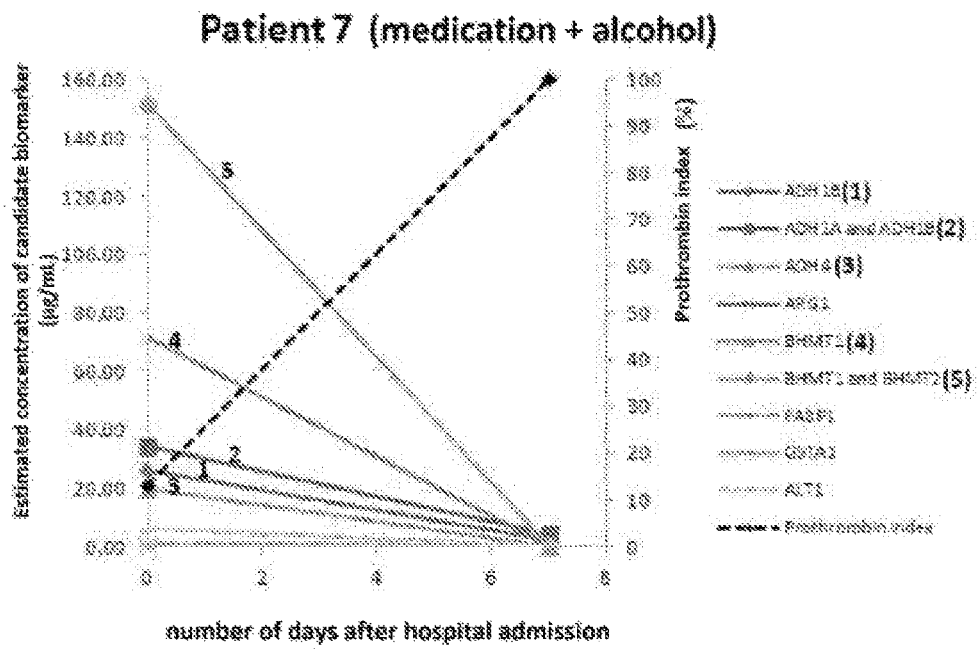
Figure 5D:
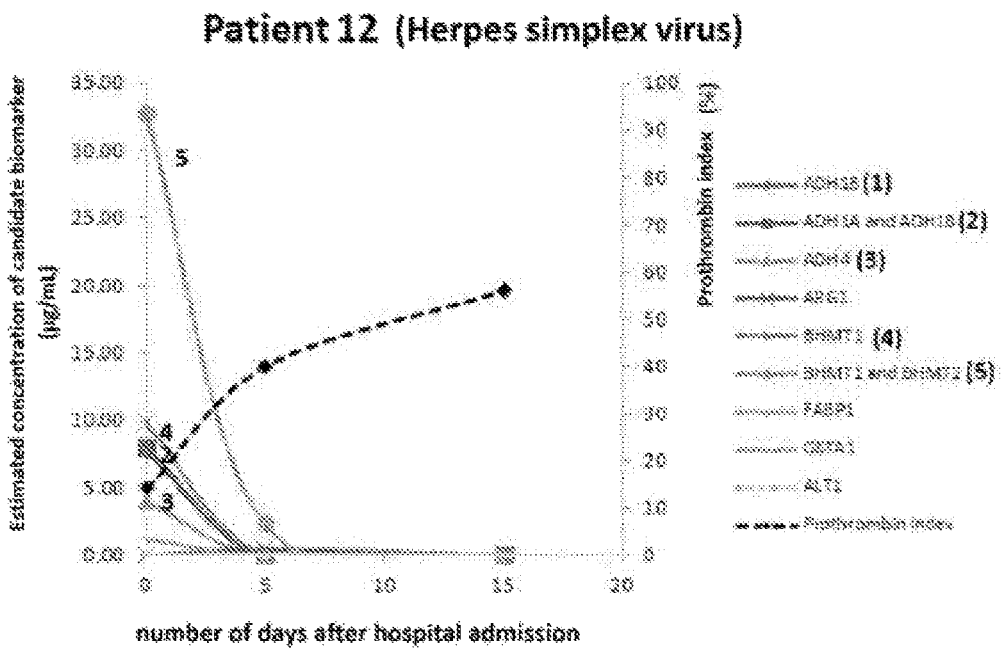
Figure 5E:
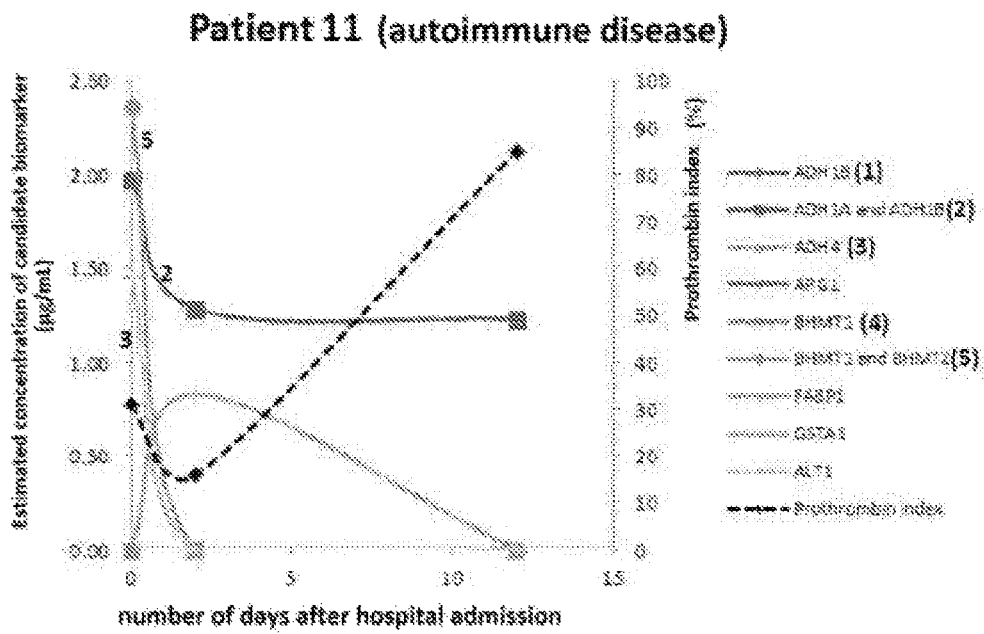
Figure 5F:
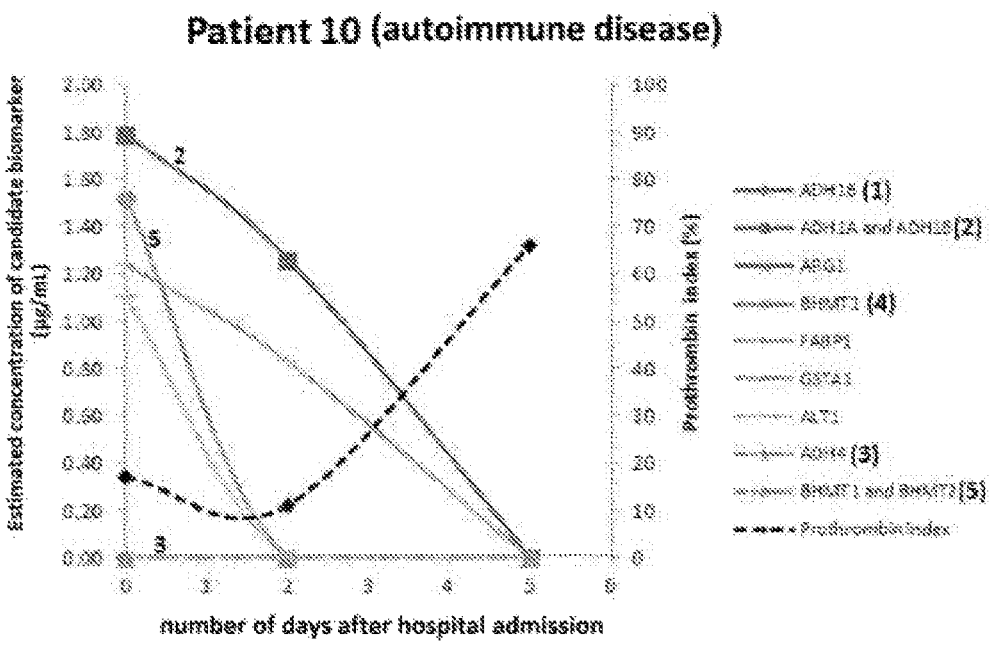

FIG. 3 shows the calibration curves obtained for ADH4, BHMT1, FABP1 and ALT1 in plasma after glycodepletion.

FIGS. 4 (A to G) describe the analysis of biomarkers in biological samples originating from patients having paracetamol-induced liver injury. The concentrations of the target biomarkers were determined using PSAQ™ standards after serum pre-fractionation by LC-SRM. The prothrombin index is mentioned as an indicator of clotting disorders and of an ALI or ALF hepatic disorder.

FIGS. 5 (A to F) describe the analysis of biomarkers in biological samples originating from patients having an ALI or ALF hepatic disorder induced by a cause other than paracetamol. The concentrations of the target biomarkers were determined using PSAQ™ standards (WO 2008/145 763 A1) after serum pre-fractionation and LC-SRM analysis. The prothrombin index is mentioned as an indicator of clotting disorders and of an ALI/ALF hepatic disorder.

Figure 6:
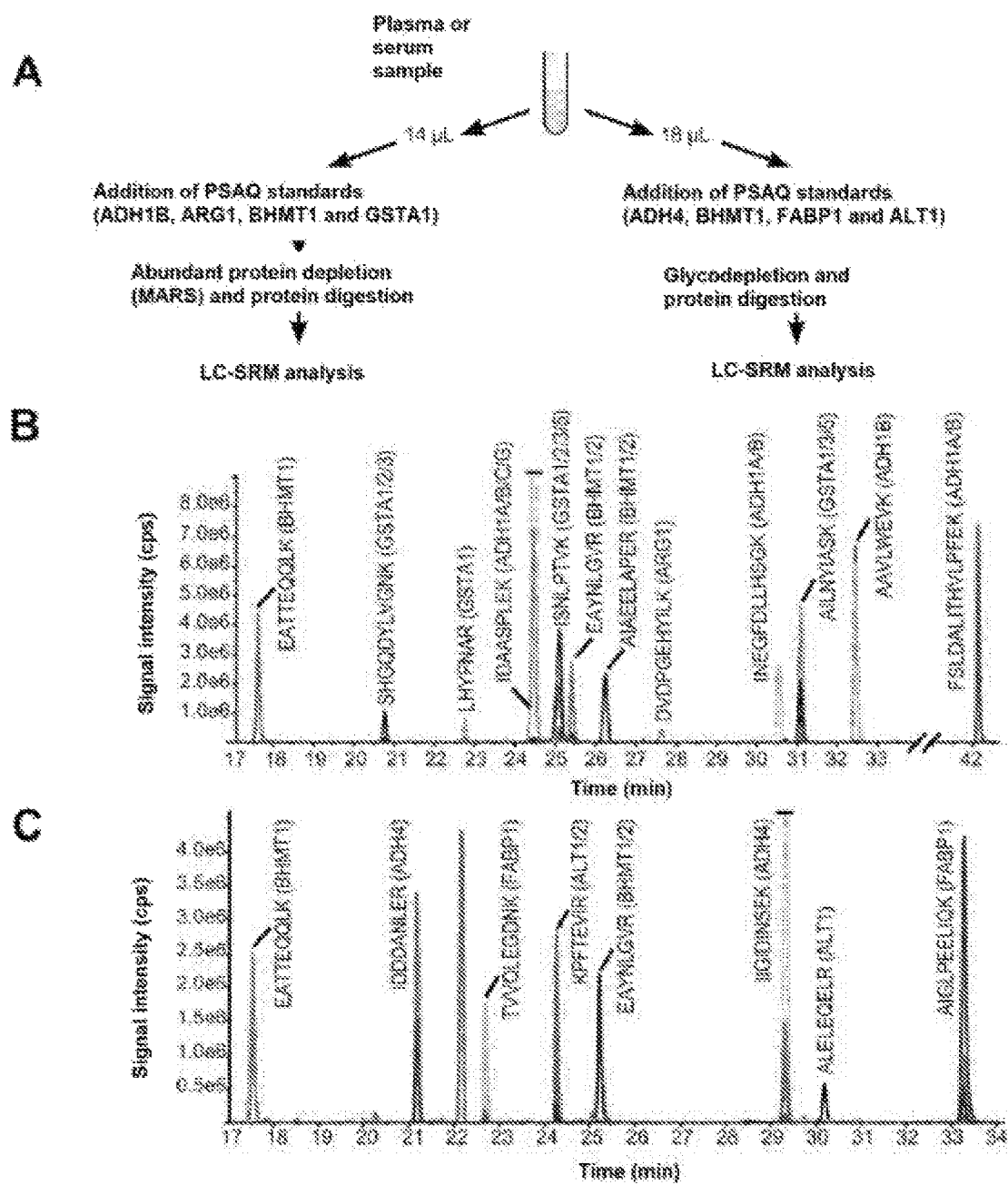

FIG. 6 describes the sample standardisation, preparation and analysis method. Panel A corresponds to the standardisation and preparation procedure. Panels B and C correspond to the signals of the various signature peptides obtained by LC-SRM analysis.

Figure 7:
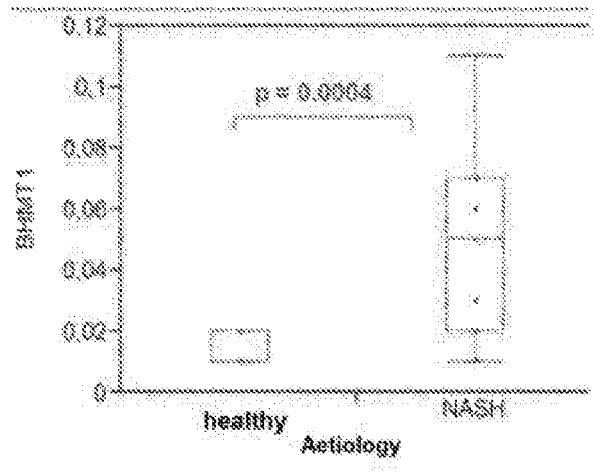
Figure 7:
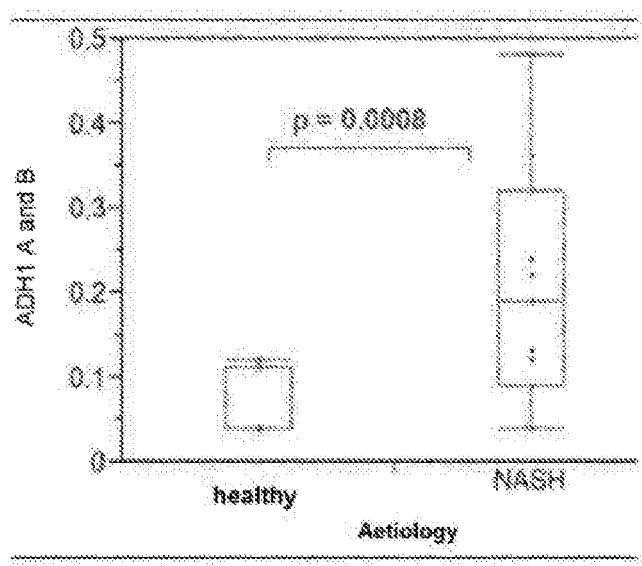

FIG. 7 shows the plasma concentrations of BHMT1 (see FIG. 7a) and the plasma concentrations of ADH1 variants A and B (see FIG. 7b) in patients suffering from non-alcoholic steatohepatitis (NASH) compared to healthy donors paired by age and sex (n=11 subjects in each group). The plasma concentrations are mentioned on the y-axis in µg/ml. A Mann-Whitney statistical test was applied with $p<0.05$ as the level of significance.

FIG. 8 shows the peptide sequences of the proteins ADH1A (SEQ ID NO. 1), ADH1B (SEQ ID NO. 2), ADH4 (SEQ ID NO. 3 & SEQ ID NO. 4), BHMT1 (SEQ ID NO. 5), BHMT2 (SEQ ID NO. 6 & SEQ ID NO. 7), ARG1 (SEQ ID NO. 8, SEQ ID NO. 9 & SEQ ID NO. 10), FABP1 (SEQ ID NO. 11), GSTA1 (SEQ ID NO. 12) and ALT1 (SEQ ID NO. 13). The analysed peptides of these target proteins are outlined in the protein peptide sequence. These peptides are peptides obtained from the digestion of the target proteins and serve as substitutes for the analysis of these proteins in mass spectrometry.

DETAILED DESCRIPTION

In the present invention, the term "hepatic disorders" or "liver disorders" or "liver lesions" denotes viral hepatitis, alcoholic hepatitis, drug-induced hepatitis, poisoning-related hepatitis such as that due to fungi or vitamins, autoimmune hepatitis, liver steatosis (NAFLD), steatohepatitis (NASH), cirrhosis and Wilson's disease, with the exclusion of hepatocarcinoma.

Within the scope of the present invention, the proteins may be assayed by any technique conventionally used by those skilled in the art such as immunological assay methods using specific antibodies or methods based on mass spectrometry. Among the assay methods based on mass spectrometry, mention may be made of AQUA technology (Gerber et al, "Absolute quantification proteins and phosphoproteins from cell lysates by tandem MS" Proc Natl Acad Sci USA. (2003) 100(12):6940-6945) or PSAQ™ (Protein Standard Absolute Quantification) technology described in the application WO 2008/145 763.

The method according to the invention is based on the detection and assay of certain biomarkers obtained from liver cell lysis; these biomarkers are proteins. According to one preferred embodiment of the invention, the assay is performed by mass spectrometry via PSAQ™ technology. According to this method, the absolute quantification of a protein by mass spectrometry requires a standard. In the present invention, the term PSAQ™ protein or PSAQ™ standard or standard protein denotes any isotopically labelled recombinant whole protein, chemically equivalent to the native protein to be assayed. The principle of the PSAQ™ method according to the invention is based on the introduction into a biological sample of a known quantity of an isotopically labelled recombinant whole standard protein, identical or equivalent (i.e. structurally similar, it may differ for example by the addition of a purification tag) to the native protein to be assayed. Unlike other absolute quantification methods, a known quantity of the standard protein is injected directly into the biological sample prior to any pre-treatment of this sample. The method according to the invention makes it possible to determine, in biological fluids such as plasma, serum, cerebrospinal fluid or urine, the concentrations of certain target proteins for which they constitute labelled analogues.

The process according to the invention is advantageously performed on a biological sample originating from a liquid specimen taken from a subject.

The process according to the invention may particularly by performed on biological fluids such as blood, serum, plasma, urine, cerebrospinal fluid, saliva, tear fluids, preferably on blood, plasma and/or serum.

PSAQ™ Standards—Standard Proteins

Numerous proteins are involved in the metabolic functions of the liver. According to the invention, the proteins suitable for characterising liver lesions are chosen according to the predominant hepatic expression thereof and the high detectability thereof in plasma, i.e. ADH1A and ADH1B, ADH4, ARG1, BHMT (sequence variants 1 and 2), FABP1, GSTA1 and ALT1.

Alcohol dehydrogenases (ADH) are oxidoreductases involved in detoxifying the body by eliminating toxic alcohols. A plurality of types of ADH exist (variants or isoforms). In respect of ADH1, there are three variants: ADH1A, ADH1B and ADH1C. These variants have been studied genetically. Duell et al. demonstrated the influence of certain genetic mutations of ADH, particularly on susceptibility to alcoholism and the risks of gastric cancer in subjects carrying these genetic mutations ("Genetic variation in alcohol dehydrogenase (ADH1A, ADH1B, ADH1C, ADH7) and aldehyde dehydrogenase (ALDH2), alcohol consumption and gastric cancer risk in the European prospective investigation into cancer and nutrition (EPIC) cohort", Carcinogenesis vol. 33, no. 2, p 361-367 (2012)).

ADH1A (SEQ ID NO. 1) and ADH1B (SEQ ID NO. 2) are involved in the oxidation of ethanol and play a major role in the catabolism of ethanol. ADH4 is involved in the oxidation of aliphatic alcohols and/or aromatic alcohols. ADH4 exists in the form of two isoforms (SEQ ID NO. 3 & SEQ ID NO. 4). In the study, the inventors looked at ADH1B but also at the mixture of the variants ADH1A and ADH1B.

BHMT (Betaine-homocysteine-methyltransferase) is a zinc-based metalloenzyme which is involved in the metabolism of homocysteine, glycine, serine, threonine and also methionine. This term BHMT denotes the sequence variants BHMT1 (SEQ ID NO. 5), BHMT2, as well as the isoforms of BHMT2 (SEQ ID NO. 6 & SEQ ID NO. 7).

Arginase ARG1 is a hydrolase; this manganese-based hepatic metalloenzyme is involved in the urea cycle. The term ARG1 denotes the three isoforms of arginase 1 (SEQ ID NO. 8, SEQ ID NO. 9 & SEQ ID NO. 10).

FABP1 ("Fatty acid-binding protein, Liver"; SEQ ID NO. 11) is liver-specific fatty acid-binding protein used to transport fatty acids from cell membranes to the mitochondria.

Glutathione S-transferases (GSTA) are enzymes which catalyse conjugation reactions of reduced glutathione (GSH) with xenobiotics in order to detoxify same. In this study, the inventors studied the variant GSTA1 (SEQ ID NO. 12) but also the pool of a plurality of variants in particular the pool of the variants GSTA1, GSTA2, GSTA3 and the pool of the 4 variants GSTA1, GSTA2, GSTA3 and GSTA5.

Cytosolic alanine aminotransferase 1 or ALT1 (SEQ ID NO. 13), also known as glutamate-pyruvate transaminase 1, is an enzyme belonging to the transaminases playing an essential role in the intermediate metabolism of glucose. This protein is known as a biomarker of liver lesions induced by certain medicinal products, alcohol, and by steatosis.

Table 1 summarises certain properties of these proteins.

The proteins ADH1A and ADH1B, ADH4, ARG1, BHMT (variants 1 and 2), FABP1, GSTA1 and ALT1 are essentially expressed in the liver. In a healthy subject, these proteins are essentially present in the liver (hepatocytes) and in some other different cell types. This is the case, for example, of the protein ADH1B which is detectable in merely three different cell types among the 80 analysed (see table 1, human protein atlas). By way of comparison and according to the human protein atlas, in healthy tissue (www.proteinatlas.org), ALT1 which is a routine marker of liver lesions is expressed in 29 cell types among the 78 analysed. The proteins ADH1A and ADH1B, ADH4, ARG1, BHMT (variants 1 and 2), FABP1, GSTA1 are therefore more liver-specific than ALT1.

TABLE 1

Biomarkers selected in the process according to the invention for monitoring hepatic disorders

| Protein (SEQ ID NO.) | Uniprot ID | Number of cell types in healthy tissue in which protein is detected (a) | Molecular mass [Da] | Biochemical function |
| --- | --- | --- | --- | --- |
| ADH1B (SEQ ID NO. 2) | P00325 | 3 out of 80 analysed | 39,855 | Xenobiotic metabolism |
| ADH1A (SEQ ID NO. 1) | P07327 | Hepatocytes | 39859 | Xenobiotic metabolism |
| ADH4 (SEQ ID NO. 3 & SEQ ID NO. 4) | P08319 | 6 out of 83 analysed | 40,222 | Xenobiotic metabolism |
| ARG1 (SEQ ID NO. 8, SEQ ID NO. 9 & SEQ ID NO. 10) | P05089 | 2 out of 83 analysed | 34,735 | Nitrogen metabolism and urea cycle |
| BHMT1 (SEQ ID NO. 5) | Q93088 | 3 out of 83 analysed | 44,998 | Homocysteine metabolism |
| FABP1 (SEQ ID NO. 11) | P07148 | 7 out of 83 analysed | 14,208 | Lipid metabolism and lipid transport |
| GSTA1 (SEQ ID NO. 12) | P08263 | 16 out of 81 analysed | 25,631 | Xenobiotic and glutathione metabolism |

(a) Source: The Human Protein Atlas (www.proteinatlas.org)

According to the invention, further biomarkers such as the protein cytokeratin 18 (CK18) may be used as a supplementary analysis in order to confirm a liver disorder and establish a diagnosis. Indeed, when hepatocytes are exposed chronically to oxidative stress and to toxic substances, they swell, store fat and exhibit disruption in the keratin filament network, and form Mallory bodies, i.e. residual clusters of microfilaments. A Mallory body is made up of abnormally phosphorylated and cross-linked keratins, such as the cytokeratin CK18. It is known that hepatocytes containing Mallory bodies are sensitive to apoptosis, inducing a significant release of CK18 proteins and Mallory bodies into the blood. The publication by Maher et al. publication de Maher et al. "Cytokeratin 18 as a non invasive marker in diagnosis of NASH and its usefulness in correlation with disease severity in Egyptian patients" published in The Egyptian Journal of Medical Human Genetics (2015) 16, p. 41 to 46, describes CK18 as a non-invasive marker suitable for correlating the concentration thereof with the degree of NASH severity. Indeed, when CK18 protein is released in the blood in whole form (M65 form), it indicates a necrotic phenomenon. When it is released in truncated form (M30 form), it indicates an apoptotic phenomenon. Generally, the blood concentrations of CK18 are measured in these two forms and the ratio between these two forms is computed. CK18 is not expressed specifically in hepatocytes, it is present in glandular epithelia.

Role of Biomarkers

In the serum or plasma of healthy patients, the proteins ADH1 (variant B or isoforms A and B) and ADH4 are present in concentrations less than 2 μg/ml, ARG1 at concentrations less than 0.3 μg/ml, FABP1 at concentrations less than 1 μg/ml, GSTA1, GSTA2, GSTA2 and GSTA5 at concentrations less than 1 μg/ml, BHMT (variants or isoforms 1 and 2) at concentrations less than 2 μg/ml and ALT1 at concentrations less than 1 μg/ml (these threshold concentrations were assessed after sample analysis according to the protocol described in FIG. 6).

The Applicant observed that the serum or plasma concentration of the proteins ADH1B, ADH1A and B, ADH4, ARG1, BHMT1 and BHMT1 and 2, FABP1, GSTA1 and ALT1 changes according to the hepatic disorder and the severity thereof.

According to the observations of the Applicant, the concentration of the proteins ADH1B, ADH1A and ADH1B, ADH4, ARG1, FABP1, GSTA1, BHMT1 and BHMT (variants 1 and 2) increase during the acute phases of liver injury induced by xenobiotics such as paracetamol, and then falls to very low levels during the liver recovery/regeneration period. These kinetics are closely correlated with those of the biological characteristics of this disease such as the prothrombin index. Some of these proteins are expressed more in the liver than others and are therefore more readily quantifiable; this is the case of the proteins ADH4, BHMT (variants 1 and 2), ADH1 (variants ADH1A and ADH1B) which may be advantageously used, individually or combined, as biomarkers for the diagnosis, monitoring and prognosis of ALI or ALF. The protein ARG1 exhibits less pronounced modifications of the plasma or serum concentration thereof, but correlated with the stage of the disorder (acute phase/recovery phase).

The markers ADH1 (ADH1B only or combination of ADH1B and ADH1A), ADH4 and BHMT (variant 1 only or combination of both variants 1 and 2) may enable early identification of liver lesions induced by medicinal products such as paracetamol, so as to adapt the patient's medical care (in particular recourse to a liver transplant). Furthermore, unlike transaminase markers (of which ALT1) and CK18 wherein the concentrations may remain elevated, these ADH1 markers (ADH1B only or combination of ADH1B and ADH1A), ADH4 and BHMT (variant 1 only or combination of both variants 1 and 2) exhibit low serum levels during spontaneous liver regeneration.

In the case of liver disorders not induced by medicinal products, a modification of the plasma/serum concentrations of the biomarkers, particularly of the proteins ADH1 (ADH1B and/or ADH1B and ADH1A), ADH4 and BHMT (variant 1 only or combination of both variants 1 and 2) is observed at lower levels than with paracetamol but it is consistent with the patient's clinical status.

According to one embodiment of the invention, the markers ADH1 (ADH1B and/or (ADH1B and ADH1A)), ADH4, ARG1, FABP1, GSTA1, ALT1 and BHMT (variant 1 and/or the mixture of both variants 1 and 2) may be used for the detection of a liver lesion.

The detection of a liver lesion may be demonstrated by the detection and/or quantification of the marker ADH1, preferably the marker ADH1B and/or the pool of ADH1A and ADH1B.

The detection of a liver lesion may be demonstrated by the detection and/or quantification of the marker ADH1 ((ADH1B and/or (ADH1B and ADH1A)) and at least one additional marker, at least two additional markers, at least three additional markers, at least four additional markers, at least five additional markers or at least six additional markers chosen among: ADH4, BHMT (variant 1 and/or combination of both variants 1 and 2), ARG1, FABP1, GSTA1 and ALT1.

The detection of a liver lesion may be demonstrated by the detection and/or quantification of two biomarkers specifically, such as ADH1 ((ADH1B and/or (ADH1B and ADH1A)) and ADH4; ADH1 (ADH1B and/or (ADH1B and ADH1A)) and BHMT (variant1 and/or a mixture of both variants 1 and 2); ADH1 (ADH1B and/or (ADH1B and ADH1A)) and ARG1; ADH1 (ADH1B and/or (ADH1B and ADH1A)) and FABP1; ADH1 (ADH1B and/or (ADH1B and ADH1A)) and GSTA1 or of the 2 biomarkers ADH1 (ADH1B and/or (ADH1B and ADH1A)) and ALT1.

The detection of a liver lesion may be demonstrated by the detection and/or quantification of three biomarkers specifically, such as ADH1 (ADH1B and/or (ADH1B and ADH1A)), ADH4 and BHMT (variant 1 and/or a mixture of both variants 1 and 2); ADH1 (ADH1B and/or (ADH1B and ADH1A)), ADH4 and ARG1; ADH1 (ADH1B and/or (ADH1B and ADH1A)), ADH4 and FABP1; ADH1 (ADH1B and/or (ADH1B and ADH1A)), ADH4 and GSTA1; ADH1 (ADH1B and/or (ADH1B and ADH1A)), ADH4 and ALT1; ADH1 (ADH1B and/or (ADH1B and ADH1A)), BHMT (variant 1 and/or a mixture of both variants 1 and 2) and ARG1; ADH1 (ADH1B and/or (ADH1B and ADH1A)), BHMT (variant 1 and/or a mixture of both variants 1 and 2) and FABP1; ADH1 (ADH1B and/or (ADH1B and ADH1A)), BHMT (variant 1 and/or a mixture of both variants 1 and 2) and GSTA1; ADH1 (ADH1B and/or (ADH1B and ADH1A)), BHMT (variant 1 and/or a mixture of both variants 1 and 2) and ALT1; ADH1 (ADH1B and/or (ADH1B and ADH1A)), ARG1 and FABP1; ADH1 (ADH1B and/or (ADH1B and ADH1A)), ARG1 and GSTA1; ADH1 (ADH1B and/or (ADH1B and ADH1A)), ARG1 and ALT1; ADH1 (ADH1B and/or (ADH1B and ADH1A)), FABP1 and GSTA1; ADH1 (ADH1B and/or (ADH1B and ADH1A)), FABP1 and ALT1 or of the 3 biomarkers ADH1 (ADH1B and/or (ADH1B and ADH1A)), GSTA1 and ALT1.

The detection of a liver lesion may be demonstrated by the detection and/or quantification of four biomarkers specifically, such as ADH1 (ADH1B and/or (ADH1B and ADH1A)), ADH4, BHMT (variant 1 and/or a mixture of both variants 1 and 2) and ARG1; ADH1 (ADH1B and/or (ADH1B and ADH1A)), ADH4, BHMT (variant 1 and/or a mixture of both variants 1 and 2) and FABP1; ADH1 (ADH1B and/or (ADH1B and ADH1A)), ADH4, BHMT (variant 1 and/or a mixture of both variants 1 and 2) and GSTA1; ADH1 (ADH1B and/or (ADH1B and ADH1A)), ADH4, BHMT (variant 1 and/or a mixture of both variants 1 and 2) and ALT1; ADH1 (ADH1B and/or (ADH1B and ADH1A)), ADH4, ARG1 and FABP1; ADH1 (ADH1B and/or (ADH1B and ADH1A)), ADH4, ARG1 and GSTA1; ADH1 (ADH1B and/or (ADH1B and ADH1A)), ADH4, ARG1 and ALT1; ADH1 (ADH1B and/or (ADH1B and ADH1A)), ADH4, FABP1 and GSTA1; ADH1 (ADH1B and/or (ADH1B and ADH1A)), ADH4, FABP1 and ALT1; ADH1 (ADH1B and/or (ADH1B and ADH1A)), ADH4, GSTA1 and ALT1; ADH1 (ADH1B and/or (ADH1B and ADH1A)), BHMT (variant 1 and/or a mixture of both variants 1 and 2), ARG1 and FABP1; ADH1 (ADH1B and/or (ADH1B and ADH1A)), BHMT (variant 1 and/or a mixture of both variants 1 and 2), ARG1 and GSTA1; ADH1 (ADH1B and/or (ADH1B and ADH1A)), BHMT (variant 1 and/or a mixture of both variants 1 and 2), ARG1 and ALT1; ADH1 (ADH1B and/or (ADH1B and ADH1A)), BHMT (variant 1 and/or a mixture of both variants 1 and 2), FABP1 and GSTA1; ADH1 (ADH1B and/or (ADH1B and ADH1A)), BHMT (variant 1 and/or a mixture of both variants 1 and 2), FABP1 and ALT1; ADH1 (ADH1B and/or (ADH1B and ADH1A)), BHMT (variant 1 and/or a mixture of both variants 1 and 2), GSTA1 and ALT1; ADH1 (ADH1B and/or (ADH1B and ADH1A)), ARG1, FABP1 and GSTA1; ADH1 (ADH1B and/or (ADH1B and ADH1A)), ARG1, FABP1 and ALT1; ADH1 (ADH1B and/ or (ADH1B and ADH1A)), ARG1, GSTA1 and ALT1 or of the four markers ADH1 (ADH1B and/or (ADH1B and ADH1A)), FABP1, GSTA1 and ALT1.

The detection of a liver lesion may be demonstrated by the detection and/or quantification of five biomarkers specifically, such as ADH1 (ADH1B and/or (ADH1B and ADH1A)), ADH4, BHMT (variant 1 and/or a mixture of both variants 1 and 2), ARG1 and FABP1; ADH1 (ADH1B and/or (ADH1B and ADH1A)), ADH4, BHMT (variant 1 and/or a mixture of both variants 1 and 2), ARG1 and GSTA1; ADH1 (ADH1B and/or (ADH1B and ADH1A)), ADH4, BHMT (variant 1 and/or a mixture of both variants 1 and 2), ARG1 and ALT1; ADH1 (ADH1B and/or (ADH1B and ADH1A)), ADH4, BHMT (variant 1 and/or a mixture of both variants 1 and 2), FABP1 and GSTA1; ADH1 (ADH1B and/or (ADH1B and ADH1A)), ADH4, BHMT (variant 1 and/or a mixture of both variants 1 and 2), FABP1 and ALT1; ADH1 (ADH1B and/or (ADH1B and ADH1A)), ADH4, BHMT (variant 1 and/or a mixture of both variants 1 and 2), GSTA1 and ALT1; ADH1 (ADH1B and/or (ADH1B and ADH1A)), ADH4, ARG1, FABP1 and GSTA1; ADH1 (ADH1B and/or (ADH1B and ADH1A)), ADH4, ARG1, FABP1 and ALT1; ADH1 (ADH1B and/or (ADH1B and ADH1A)), ADH4, ARG1, GSTA1 and ALT1; ADH1 (ADH1B and/or (ADH1B and ADH1A)), ADH4, FABP1, GSTA1 and ALT1; ADH1 (ADH1B and/or (ADH1B and ADH1A)), BHMT (variant 1 and/or a mixture of both variants 1 and 2), ARG1, FABP1 and GSTA1; ADH1 (ADH1B and/or (ADH1B and ADH1A)), BHMT (variant 1 and/or a mixture of both variants 1 and 2), ARG1, FABP1 and ALT1; ADH1 (ADH1B and/or (ADH1B and ADH1A)), BHMT (variant 1 and/or a mixture of both variants 1 and 2), ARG1, GSTA1 and ALT1; ADH1 (ADH1B and/or (ADH1B and ADH1A)), BHMT (variant 1 and/or a mixture of both variants 1 and 2), FABP1, GSTA1 and ALT1 or the five biomarkers ADH1 (ADH1B and/or (ADH1B and ADH1A)), ARG1, FABP1, GSTA1 and ALT1.

The detection of a liver lesion may be demonstrated by the detection and/or quantification of six biomarkers specifically, such as ADH1 (ADH1B and/or (ADH1B and ADH1A)), ADH4, BHMT (variant 1 and/or a mixture of both variants 1 and 2), ARG1, FABP1 and GSTA1; ADH1 (ADH1B and/or (ADH1B and ADH1A)), ADH4, BHMT (variant 1 and/or a mixture of both variants 1 and 2), ARG1, FABP1 and ALT1; ADH1 (ADH1B and/or (ADH1B and ADH1A)), ADH4, BHMT (variant 1 and/or a mixture of both variants 1 and 2), ARG1, GSTA1 and ALT1; ADH1 (ADH1B and/or (ADH1B and ADH1A)), ADH4, BHMT (variant 1 and/or a mixture of both variants 1 and 2), FABP1, GSTA1 and ALT1; ADH1 (ADH1B and/or (ADH1B and ADH1A)), ADH4, ARG1, FABP1, GSTA1 and ALT1 or the six biomarkers ADH1 (ADH1B and/or (ADH1B and ADH1A)), BHMT (variant 1 and/or a mixture of both variants 1 and 2), ARG1, FABP1, GSTA1 and ALT1;

The detection of a liver lesion may be demonstrated by the detection and/or quantification of seven biomarkers specifically i.e. ADH1 (ADH1B and/or (ADH1B and ADH1A)), ADH4, BHMT (variant 1 and/or a mixture of both variants 1 and 2), ARG1, FABP1, GSTA1 and ALT1.

In one particular embodiment, in addition to the marker ADH1 (ADH1B and/or ADH1A)), the marker ADH4 and/or BHMT will be preferentially used; in the case of liver lesions, the plasma/serum concentration of ADH4 and that of BHMT is elevated and readily quantifiable.

In one preferred embodiment, the detection of a liver lesion is demonstrated by the detection and/or quantification of the three biomarkers ADH1 (ADH1B and/or ADH1A)), ADH4 and BHMT (variant 1 and/or a mixture of both variants 1 and 2).

In a preferred embodiment, the liver lesions may be detected by analysing three biomarkers among the proteins: ADH1 (ADH1B and/or ADH1A)), ADH4, ARG1, FABP1, GSTA1, ALT1 and BHMT (variant 1 and/or combination of both variants 1 and 2).

Advantageously, the more the detection of a liver lesion involves biomarkers, the more the analysis of the liver disorder will be enhanced.

Process for the Specific Detection and Absolute Quantification of Protein Biomarkers The specific detection and absolute quantification of protein biomarkers in biological fluids may be carried out in different ways. In a medical testing laboratory, biomarkers are routinely detected and quantified using immunological processes. This infers the availability of an antibody binding specifically with the protein to be assayed. Mass spectrometry makes it possible to detect and assay molecules, and more particularly peptides, directly and without having an antibody. As such mass spectrometry techniques have been developed over the last decade, particularly methods known as the acronyms SRM ("Selected Reaction Monitoring") and MRM ("Multiple Reaction Monitoring") making it possible to quantify one or a plurality of target molecules in a complex biological sample.

However, absolute quantification (i.e. the determination of the concentration of the target molecules) by mass spectrometry requires quantification standards. It is possible to use different types of quantification standards which may correspond to isotopically labelled peptides, labelled peptide concatemers, isotopically labelled protein fragments or isotopically labelled whole proteins (see the publications Brun et al, "Isotope dilution strategies for absolute quantitative proteomics." Journal of Proteomics (2009) 72(5) pages 740-749 and Zeiler et al, "A Protein Epitope Signature Tag (PrEST) library allows SILAC-based absolute quantification and multiplexed determination of protein copy numbers in cell lines." Molecular and Cellular Proteomics (2012) 11(3): 0111.009613). In any case, the standards generate or correspond to signature peptides which are peptides obtained from the digestion of the target proteins and which serve as substitutes for the analysis of these proteins in mass spectrometry (the preparation and analysis of the signature peptides are described hereinafter). Among these quantification approaches, and as mentioned in the document WO 2008/145 763 A1, the combined use of mass spectrometry in SRM or MRM mode and of standard proteins, isotopically labelled analogues of the target biomarkers (PSAQ™ standards) and introduced in a known quantity into a sample, makes it possible to specifically detect and accurately and precisely quantify, in this sample, the target biomarkers.

The term "homologous isotopically labelled protein of the targeted marker or target biomarker" or "standard protein" denotes any protein possessing the same amino acid sequence as the native protein that it is sought to assay and certain atoms whereof are replaced by atoms labelled with stable isotopes. Advantageously, certain specific amino acids may be isotopically labelled, such as arginine and lysine. In this case, the arginine and lysine residues of the standard proteins are uniformly labelled with carbon and nitrogen isotopes, i.e. $^{13}C$ and $^{15}N$. According to the invention, advantageously, the standard is introduced into the biological sample such that the final concentration thereof in the biological sample is between 0.5 and 5 µg/mL, for acute liver diseases such as ALI or ALF. In the case of non-alcoholic or alcoholic steatohepatitis, the standard is introduced at a concentration between 20 and 200 ng/mL. According to the nature of the targeted protein, optimal concentrations for calibration have been determined for each of the standard proteins and presented hereinafter in table 2.

TABLE 2

Optimal concentration (µg/mL) of standard protein in biological sample by standard protein type (case of ALI/ALF acute hepatic disorders)

| Standard protein (PSAQ ™ standard) | Optimal concentration (µg/mL) of standard protein in biological sample |
|---|---|
| ARG1 | 1 |
| BHMT1 | 2 |
| GSTA1 | 1 |
| ADH1B | 3 |
| ADH4 | 2 |
| FABP1 | 1 |
| ALT1 | 3 |

In one preferred embodiment of the invention, the biomarkers are not detected directly but by means of peptide subunits, referred to as "signature peptides". The term "signature peptide" denotes herein any peptide having an amino acid sequence between 5 and 30 amino acids, which is included in the sequence of the marker to be analysed, suitable for specifically identifying in a biological sample the presence of said marker. Advantageously, these signature peptides are generated by enzymatic or chemical digestion of the sample or of a fraction thereof, as explained in more detail hereinafter. More particularly, the selected biomarkers are identified by detecting proteolytic peptides obtained after digesting proteins contained in the biological sample, i.e. signature peptides suitable for quantifying the markers in the biological sample, as mentioned in the document WO 2008/145 763 A1. These signature peptides are suitable for monitoring these biomarkers and in particular the predominant isoforms thereof in the liver. Indeed, certain signature peptides (see FIG. 8) are shared between a plurality of isoforms, such as ADH1 where the signature peptide INEGFDLLHSGK is suitable for monitoring both ADH1B and ADH1A, such as BHMT with the isoforms BHMT1 and BHMT2 or GSTA with the isoforms GSTA1, GSTA2, GSTA3 or GSTA5 (see table 3, FIG. 8).

TABLE 3

Signature peptides of the biomarkers used in the process according to the invention and generated by digestion with trypsin or a mixture of trypsin and endolysC

| Biomarker of interest | Signature peptide of marker of interest | Peptide sequence identification (SEQ ID NO.) | Peptide specificity with respect to biomarker |
|---|---|---|---|
| ADH1B | AAVLWEVK | SEQ ID NO. 17 | specific |
| ADH1B | INEGFDLLHSGK | SEQ ID NO. 16 | peptide present in ADH1A and ADH1B |
| ADH1B | FSLDALITHVLPFEK | SEQ ID NO. 15 | peptide present in ADH1A and ADH1B |
| ADH1B | IDAASPLEK | SEQ ID NO. 14 | peptide present in ADH1A, ADH1B, ADH1C and ADH1G |
| ADH4 | FNLDALVTHTLPFDK | SEQ ID NO. 20 | specific |
| ADH4 | IDDDANLER | SEQ ID NO. 18 | specific |
| ADH4 | IIGIDINSEK | SEQ ID NO. 19 | specific |
| ARG1 | DVDPGEHYILK | SEQ ID NO. 25 | specific |
| ARG1 | TIGIIGAPFSK | SEQ ID NO. 24 | specific |
| ARG1 | EGLYITEEIYK | SEQ ID NO. 26 | specific |
| BHMT1 | EATTEQQLK | SEQ ID NO. 21 | specific |
| BHMT1 | AIAEELAPER | SEQ ID NO. 23 | peptide present in BHMT1 and BHMT2 |
| BHMT1 | EAYNLGVR | SEQ ID NO. 22 | peptide present in BHMT1 and BHMT2 |
| FABP1 | AIGLPEELIQK | SEQ ID NO. 27 | specific |
| FABP1 | FTITAGSK | SEQ ID NO. 28 | specific |
| FABP1 | TVVQLEGDNK | SEQ ID NO. 29 | specific |

TABLE 3-continued

Signature peptides of the biomarkers used in the process according to the invention and generated by digestion with trypsin or a mixture of trypsin and endolysC

| Biomarker of interest | Signature peptide of marker of interest | Peptide sequence identification (SEQ ID NO.) | Peptide specificity with respect to biomarker |
|---|---|---|---|
| GSTA1 | LHYFNAR | SEQ ID NO. 30 | specific |
| GSTA1 | SHGQDYLVGNK | SEQ ID NO. 31 | peptide present in GSTA1, GSTA2 and GSTA3 |
| GSTA1 | ISNLPTVK | SEQ ID NO. 33 | peptide present in GSTA1, GSTA2, GSTA3 and GSTA5 |
| GSTA1 | AILNYIASK | SEQ ID NO. 32 | peptide present in GSTA1, GSTA2, GSTA3 and GSTA5 |
| ALT1 | ALELEQELR | SEQ ID NO. 34 | specific |
| ALT1 | LLVAGEGHTR | SEQ ID NO. 35 | specific |
| ALT1 | KPFTEVIR | SEQ ID NO. 36 | peptide present in ALT1 and ALT2 |

After introduction into a biological sample of a known quantity of PSAQ™ standard protein, identical or structurally very similar to the native protein that it is sought to assay, a digestion step, enzymatic or chemical, may be carried out so as to obtain the proteolytic peptides of the proteins initially present in the sample including the signature peptides of the target biomarkers readily identifiable and quantifiable by LC-MS in SRM or MRM mode. It is also possible to use, instead of the PSAQ standards, isotopically labelled peptide standards (referred to as AQUA peptides for "Absolute quantification" or SIL peptides for "Stable Isotope Labelling"). These labelled standard peptides have an identical sequence to the signature peptides monitored and they are added into the sample immediately before or immediately after the protein digestion step. These standards enable absolute quantification of the target proteins but which is frequently less accurate than quantification using the PSAQ method.

Advantageously, the digestion of the proteins is performed enzymatically, and more particularly in the presence of a trypsin solution or indeed a mixture of trypsin and EndolysC. The quantity of enzyme used for digestion corresponds generally to an enzyme/protein ratio (by weight) of 1:100 to 1:10. After adding the enzyme sample into the biological sample and incubating at 37° C., so as to generate the proteolytic peptides, the digestion is stopped by adding at least a sufficient quantity of formic acid into the biological sample. The term "proteolytic peptide" denotes any peptide or amino acid sequence obtained from the degradation of a polypeptide, particularly by enzymatic or chemical digestion of said polypeptide.

The proteolytic peptides (including the signature peptides and isotopically labelled peptides) obtained in this way are subsequently analysed by LC-MS. Note that it is possible to use different types of enzymes to carry out protein digestion. According to the cleavage specificity of the selected enzyme, the signature peptides suitable for detecting and quantifying the target proteins will be different. These signature peptides may be predicted by performing in silico digestion of the target proteins (the amino acid sequence whereof is known). The detectability in mass spectrometry thereof is subsequently verified experimentally. Table 3 lists signature peptides obtained and monitored after digestion with trypsin or a mixture of trypsin and endolysC. EndolysC is an endoproteinase Lys-C.

So as to facilitate the isolation and identification of the proteins present in the biological samples, a pre-treatment step of the biological sample may advantageously be carried out. Indeed, this step makes it possible to remove at least partially the non-targeted abundant proteins present in the biological sample and thereby increase the sensitivity of detection of the target biomarkers while retaining the integrity of the PSAQ™ standard (standard protein) and of the target biomarker.

Figure 1:
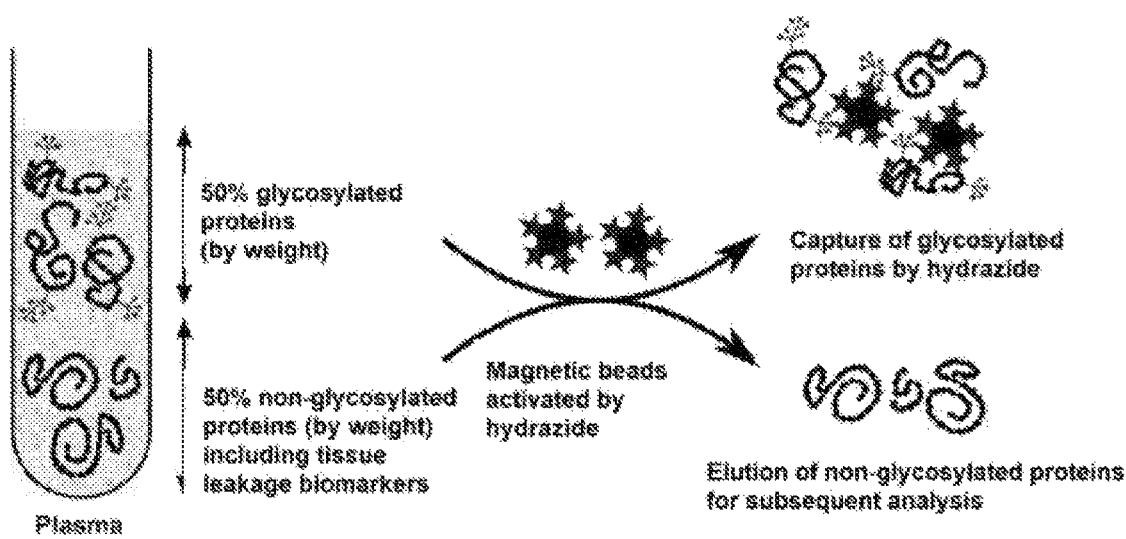

So as to retain, in the course of the process, the integrity of the target biomarkers and of the PSAQ™ standards, a plurality of pre-treatment modes may be used, such as the depletion of abundant proteins using an affinity chromatography device (immunodepletion), a chemical reagent having an affinity for albumin (cibacron blue type) or a process for glycodepletion of the biological sample (see FIG. 1). These pre-treatment methods are known per se.

Abundant protein depletion is an affinity method suitable for extracting at least partially the majority proteins from serum, i.e. abundant proteins such as albumin, IgG, transferrin or IgA.

Glycodepletion is a method suitable for capturing and extracting at least partially the glycoproteins present in the biological sample so as to leave in the biological sample the other proteins such as the target biomarkers which are not glycosylated. In the process which is the subject of the diagram according to FIG. 1, the glycoproteins are captured by magnetic beads functionalised with hydrazide.

In order to avoid performing a sensitive detection and an exact quantification of the target biomarkers, a suitable sample pre-treatment mode for each biomarker is chosen. As such, the proteins ARG1, ADH1 (variant A and B), BHMT (variants 1 and 2) and GSTA1 will be preferentially treated by abundant protein depletion by affinity chromatography and the proteins ADH4, FABP1, ALT1 and BHMT by glycodepletion.

After treating the biological sample, an additional biological sample treatment step may be performed by electrophoresis. This step makes it possible to refine the extraction of the proteins of interest. This electrophoresis step may be performed on acrylamide gel. In this case, the enzymatic digestion is also performed in gel.

An additional enrichment step of the target peptides by immunoaffinity prior to any analysis by LC-MS in SRM or MRM mode may advantageously be carried out. This helps facilitate the detection and quantification of these peptides by mass spectrometry.

The proteolytic peptides are subsequently analysed by LC-MS in SRM mode. Calibration curves were produced for each biomarker so as to assess the analytical performances of the assay and ensure the reliability of the quantification of the target biomarkers in the biological sample. The calibration curves were produced using samples containing an increasing quantity of non-labelled protein and a constant quantity of PSAQ™ standard protein, these samples having undergone the same treatments as the biological sample wherein it is sought to detect and quantify a target biomarker, i.e. pre-treatments and/or a digestion. Blanks containing merely endogenous proteins are also produced. All the calibration points are performed several times for reproducibility purposes (see FIGS. 2 and 3).

The quantification results obtained for the various signature peptides of each target biomarker are consistent and demonstrate that the process according to the invention makes it possible to detect and quantify target biomarkers with precision. The quantification results are shown hereinafter in table 4 for each biomarker and for each signature peptide obtained after immunodepletion or glycodepletion. Table 4 shows the lower limit of detection (LLD) of the various proteins determined by the calibration curves described above and the lower limit of quantification (LLQ) defined as being equal to 3 times the LLD.

The LC-SRM analyses were carried out on a QTRAP type mass spectrometer in a range from 400 to 1000 m/z. Prior to any analysis, the proteolytic peptides may be concentrated on a pre-column and separated on a liquid chromatography column in gradient mode so as to facilitate the subsequent analysis.

The identification of the peaks of each peptide was carried out using Skyline software, known to mass spectrometry specialists. In addition to the evaluation of the peptide signal (composite signal), all the transitions are inspected individually and excluded if they are deemed unsuitable for quantification (poor signal-to-noise ratio, obvious interferences). The ratios of the peak areas relative to the labelled and non-labelled peptides are computed for each SRM transition. These ratios are subsequently used to determine the corresponding mean ratio, and finally the mean ratio of the abundance of the target protein is computed on the basis of the ratios obtained for the various signature peptides. The concentration of the biomarkers was subsequently computed on the basis of the mean ratio obtained for each of the proteins. The lower limit of detection (LLD) was determined according to the calibration curve method and the lower limit of quantification (LLQ) is defined as being equal to 3 times the LLD. L'. For each patient, the concentration of the target biomarkers is determined at different times t during their hospitalization.

TABLE 4

| Analytical performance of the test for each target biomarker (limit of detection). | | | | | | | |
|---|---|---|---|---|---|---|---|
| Protein | Signature peptide | Biochemical method | Tested concentration range [ug/ml] | Precision [%] | LLD [μg/ml] | LLQ [μg/ml] | Precision at LLQ (CV in %) |
| ADH1B | INEGFDLLHSGK | MARS | 0.81–73.5 | 79 | 10.66 | 31.99 | 41 |
|  | IDAASPLEK |  |  | 95 | 0.72 | 2.17 | 22–26 |
|  | FSLDALITHVLPFEK |  |  | 97 | 0.77 | 2.30 | ND |
|  | AAVLWEVK |  |  | 112 | 2.01 | 2.30 | 3–13 |
| ARG1 | DVDPGEHYILK | MARS | 0.04–1.50 | 146 | 0.31 | 0.94 | 9 |
|  | TIGIIGAPFSK |  |  | 118 | 0.30 | 0.90 | 4–8 |
|  | EGLYITEEIYK |  |  | 138 | 0.31 | 0.92 | 6.15 |
| BHMIT1 | AIAEELAPER | MARS | 1.50–145.8 | 114 | 1.38 | 4.15 | 12–19 |
|  | EAYNLGVR |  |  | 88 | 3.49 | 10.48 | 15–40 |
|  | EATTEQQLK |  |  | 83 | 2.04 | 6.11 | 6–15 |
| GSTA1 | ISNLPTVK | MARS | 0.09–3.43 | 121 | 0.30 | 0.91 | 6–10 |
|  | LHYFNAR |  |  | 132 | 0.32 | 0.97 | 10–14 |
|  | AILNYIASK |  |  | 124 | 0.29 | 0.87 | 7–10 |
|  | SHGQDYLVGNK |  |  | 125 | 0.41 | 1.24 | 9–11 |
| ADH4 | FNLDALVTHTLPFDK | Glycodepletion | 0.25–24.8 | 139 | 1.59 | 4.77 | 9–16 |
|  | IDDDANLER |  |  | 148 | 1.75 | 5.25 | 8–10 |
|  | IIGIDINSEK |  |  | 136 | 1.60 | 4.81 | 0–8 |
| BHMT1 | AIAEELAPER | Glycodepletion | 0.60–79.5 | 143 | 6.53 | 19.58 | 8 |
|  | EAYNLGVR |  |  | 151 | 4.15 | 12.45 | NA |
|  | EATTEQQLK |  |  | 136 | 6.17 | 18.52 | 2–6 |

TABLE 4-continued

Analytical performance of the test for each target biomarker (limit of detection).

| Protein | Signature peptide | Biochemical method | Tested concentration range [ug/ml] | Precision [%] | LLD [µg/ml] | LLQ [µg/ml] | Precision at LLQ (CV in %) |
|---|---|---|---|---|---|---|---|
| FABP1 | AIGLPEELIQK | Glyco-depletion | 0.18-3.69 | 110 | 0.71 | 2.13 | 2-13 |
|  | FTITAGSK |  |  | 114 | 0.64 | 1.91 | 5-14 |
|  | TVVQLEGDNK |  |  | 108 | 0.66 | 1.99 | 1-8 |
| ALT1 | ALELEQELR | Glyco-depletion | 0.40-8.10 | 96 | 1.21 | 3.62 | 6-14 |
|  | LLVAGEGHTR |  |  | 92 | 1.10 | 3.29 | 15 |
|  | KPFTEVIR |  |  | 117 | 2.17 | 6.52 | 9-10 |

In patients suffering from acute liver injury (ALI) or failure (ALF), serum concentrations of biomarkers (in particular ADH1B, ADH1A and ADH1B, ADH4 and BHMT1, BHMT1 and BHMT2) rise rapidly during the acute phase and fall to very low levels during liver regeneration (FIGS. 4 and 5). These serum kinetics are correlated with the progression of conventional biological monitoring parameters (clotting parameters, transaminases, and CK18) but the concentrations of the biomarkers ADH1B, ADH and ADH1A, ADH4, BHMT1, BHMT1 and BHMT2 are restored earlier. These results suggest that these biomarkers may be very useful for enhancing the biological monitoring of the patient, assessing the prognosis earlier (liver regeneration or worsening) and assisting with the liver transplant decision. In the case of paracetamol-induced acute or fulminant hepatitis, the rapid and strong increases in the serum concentrations of the biomarkers may be useful for the early identification of the aetiology, which is decisive for the rapid administration of treatment and a favourable prognosis.

These biomarkers may also be used for assessing the toxicity of chemical molecules (candidate medicinal products), medicinal products (pharmacovigilance) or other xenobiotics on humans or on animal models, or on in vitro models (liver cell line cultures). In humans and animals, the assay may be performed on biological fluids. In the case of in vitro models, this assay will be performed using the culture medium.

Examples

The invention is illustrated hereinafter by examples which however do not restrict the invention. These examples relate to a method for in vitro diagnosis of hepatic disorders from a biological sample and the use thereof, particularly for detecting acute liver injury or non-alcoholic steatohepatitis in a patient.

Standard Protein Preparation

Non-labelled recombinant proteins were purchased from Abcam. Isotopically labelled proteins (PSAQ™ standards) were synthesised using: either an acellular protein expression system in the presence of [$^{13}C_6$, $^{15}N_2$] L-lysine and [$^{13}C_6$, $^{15}N_4$] L-arginine (Eurisotop, Saint Aubin, France), as described in the publication by Lebert et al., "Production and use of stable isotope-labelled proteins for absolute quantitative proteomics" published in Methods in Molecular Biology vol. 753, p. 93-115 (2011), i.e. an expression system corresponding to an *Escherichia coli* strain auxotrophic for lysine and arginine as described in the article by Picard et al., "PSAQ™ standards for accurate MS-based quantification of proteins: from the concept to biomedical applications" J Mass Spectrom. 2012; 47(10), p. 1353-1363.

The purity of the standard proteins was verified (>95% purity) and quantified by amino acid analysis as described in the publication by Louwagie et al. "Introducing AAA-MS, a rapid and sensitive method for amino acid analysis using isotope dilution and high-resolution mass spectrometry" published in Journal of Proteome Research vol. 11, p 3929-3936 (2012). For this purpose, the PSAQ™ proteins were hydrolysed in an acid process in the presence of a known quantity of a reference protein bovine serum albumin supplied by the National Institute of Standards and Technology (United States). The amino acids originating from the PSAQ™ proteins were quantified by high-resolution mass spectrometry by comparing the signals emitted by the labelled amino acids originating from the PSAQ™ protein and the non-labelled analogues thereof originating from the bovine serum albumin. The incorporation of isotopically labelled amino acids, as determined by LC-MS and LC-SRM (liquid chromatography-mass spectrometry in selected reaction monitoring mode), was greater than 99%.

Preparation of a Biological Sample

Thirteen patients with acute liver injury (ALI) were recruited at the hepatology department of Hôpital Paul Brousse (Villejuif, France). The acute liver injury of these patients was detected by elevated transaminase activity reflecting the active liver cell lysis present in these patients' blood, clotting disorders with an INR (International Normalised Ratio)>1.5 and by the absence in these patients of pre-existing liver disease.

Among these patients, four presented with hepatic encephalopathy (grade>=1) in less than 26 weeks after the onset of the symptoms and were categorised as ALF patients (see table 5). Serum samples from these patients were supplied by the Biological Resources Centre of the Paris-Sud Faculty of Medicine, France (accreditation number: 2011/39938). Etablissement Français du Sang (Etablissement Français du Sang, La Tranche, France) supplied seven anonymous serum samples from healthy donors. These serum samples were subsequently collected in untreated tubes (BD Biosciences, Le Pont de Claix, France) and were centrifuged at 1000 g for 15 min to obtain the serum. Serum samples were aliquoted and immediately frozen at −80° C. prior to any subsequent use. For each patient, multiple serum samples were taken at multiple sampling days during hospitalization. Analyses were conducted on each patient so as to ensure that these patients did not suffer from hepatitis A, B and/or C virus. All the patients were screened for hepatitis A, B and C virus (HAV, HBV, HCV) and were found to be negative for all these viruses. The biological parameters of the liver injury (INR, prothrombin time (PT), transaminase, bilirubin, platelet and creatinine levels) were determined using standard methods. The levels of soluble CK18 protein and of cleaved caspase-cytokeratin 18 protein (CK18Asp396) present in the serum were measured using ELISA M65 and M30Apoptosense kits (Peviva, Sweden). The calibration curves were determined using human plasma purchased from Sigma Aldrich (Saint Quentin Fallavier, France).

previously sampled from a subject, whether they were a carrier of acute liver injury or a healthy donor so as to be able to quantify the presence of the proteins in the subject's serum. The serum-PSAQ™ solution was then left incubated for 1 hour at 4° C. under gentle stirring.

The sample comprising serum (or plasma) and the PSAQ™ proteins were deposited on an affinity column suitable for extracting the six most abundant proteins (Albumin, IgG, Transferrin, IgA, haptoglobin and antitrypsin) in

TABLE 5

Clinical and biological characteristics of patients suffering from ALI (Acute liver injury) or ALF

| Patient number | Sample collection at x d after hospitalisation | Aetiology | Sex | Age (years) | ALT activity (U/L) | PI* (%) | INR ** | ALI or ALF ** | Outcome | CK18 (U/L) | CK18 Asp396 (U/L) |
|---|---|---|---|---|---|---|---|---|---|---|---|
| 1 | 0 | Paracetamol | F | 20 | 1489 | 9 | 16 | ALI | Alive | 13800 | 3333 |
|   | 10 |   |   |   | 402 | 59 | 1.42 |   |   | 1048 | 944 |
| 2 | 0 | Paracetamol | F | 29 | 634 | 19 | 4.8 | ALF | Alive | N/A | N/A |
|   | 2 |   |   |   | 4565 | 17 | 5.45 |   |   | N/A | N/A |
|   | 3 |   |   |   | 8118 | 18 | 4.73 |   |   | N/A | N/A |
| 3 | 0 | Paracetamol | F | 24 | 6410 | 21 | 3.82 | ALI | Alive | 22243 | 5691 |
|   | 3 |   |   |   | 2295 | 66 | 1.31 |   |   | 1618 | 479 |
| 4 | 0 | Paracetamol | F | 18 | 2653 | 31 | 2.6 | ALI | Alive | 19806 | 7212 |
|   | 2 |   |   |   | 1900 | 57 | 1.45 |   |   | 1618 | 479 |
| 5 | 0 | Paracetamol | M | 25 | 173 | 41 | 1.99 | ALI | Alive | N/A | N/A |
|   | 2 |   |   |   | 2571 | 26 | 3.21 |   |   | N/A | N/A |
|   | 6 |   |   |   | 683 | 75 | 1.2 |   |   | N/A | N/A |
| 6 | 0 | Paracetamol | F | 23 | 770 | 39 | 2.06 | ALI | Alive | 5138 | 1379 |
|   | 1 |   |   |   | 7165 | 18 | 4.8 |   |   | 23088 | 8938 |
|   | 5 |   |   |   | 1831 | 89 | 1.07 |   |   | 956 | 529 |
| 7 | 0 | Medication + alcohol | M | 24 | 7300 | 13 | 7.47 | ALI | Alive | 12138 | 5350 |
|   | 7 |   |   |   | 481 | 100 | 0.89 |   |   | 631 | 338 |
| 8 | 0 | Paracetamol | F | 16 | 15480 | 20 | 4.17 | ALI | Alive | 21363 | 533 |
|   | 4 |   |   |   | NA | 68 | 1.3 |   |   | 600 | 254 |
| 9 | 0 | Paracetamol + alcohol | M | 57 | 2710 | 16 | 5.53 | ALF | Deceased (sepsis) | 23025 | 15288 |
|   | 2 |   |   |   | NA | 42 | 1.97 |   |   | 9956 | 1117 |
|   | 7 |   |   |   | NA | 51 | 1.65 |   |   | 2000 | 421 |
| 10 | 0 | autoimmune disease | F | 58 | 2224 | 17 | 5.76 | ALF | Alive | 15638 | 9933 |
|   | 2 |   |   |   | 1861 | 11 | 10.69 |   |   | 15013 | 7275 |
|   | 5 |   |   |   | NA | 66 | 1.3 |   |   | 1275 | 450 |
| 11 | 0 | autoimmune disease | M | 56 | 2170 | 31 | 2.52 | ALI | Alive | 23056 | 15117 |
|   | 2 |   |   |   | 1119 | 16 | 5.59 |   |   | 6400 | 2417 |
|   | 12 |   |   |   | NA | 85 | 1.11 |   |   | 2256 | 617 |
| 12 | 0 | Herpes simplex virus | F | 22 | 1383 | 14 | 6.52 | ALF | Alive | 11669 | 4863 |
|   | 5 |   |   |   | 153 | 40 | 2.07 |   |   | 11388 | 4029 |
|   | 15 |   |   |   | 133 | 56 | 1.1 |   |   | 1088 | 229 |
| 13 | 0 | Medication | F | 32 | 892 | 28 | 2.8 | ALI | Alive | 14781 | 7458 |
|   | 2 |   |   |   | 984 | 54 | 1.58 |   |   | 3463 | 938 |
|   | 3 |   |   |   | 589 | 80 | 1.15 |   |   | 1856 | 375 |

Process for In Vitro Diagnosis of Liver Disorders by the Presence and Quantification of a Marker of Interest The PSAQ™ standard protein is injected directly into the biological sample (serum) prior to any pre-treatment. This approach makes it possible to determine, in biological fluids such as plasma, serum, spinal fluid or urine, the concentrations of certain target proteins such as biomarkers of diseases for which they constitute labelled analogues. A number of pre-treatment methods such as abundant protein depletion (by immunoaffinity or affinity with a chemical reagent) and glycodepletion of the biological sample were envisaged as to retain, during the process, the integrity of the PSAQ™ proteins. As such, the proteins ARG1, ADH1B, BHMT1 and GSTA were subjected to abundant protein depletion according to Agilent Technologies MARSX technology and the proteins ADH4, FABP1, ALT1 and BHMT1 to glycodepletion.

Abundant Protein Depletion

Prior to any pre-treatment, defined quantities of PSAQ™ protein (see table 2) were added to 14 μl of serum or plasma serum (MARS technology, spin cartridge from Agilent Technologies, Les Ulis, France) according to the manufacturer's instructions. This method is suitable for extracting almost 85 to 90% of all of the proteins present in serum.

Following the passage of the serum (or plasma) on the MARS affinity column, the serum samples thereby free from albumin, IgG, transferrin, IgA, haptoglobin and antitrypsin were concentrated up to a volume of 50 μl on an ultrafiltration device having an exclusion limit of 3000 Da (Merck Milliport, Molsheim, France). A solution of 4 M urea and of $NH_4HCO_3$ at 50 mM was deposited on the sample in the ultrafiltration device so as to exchange the buffer.

The resulting low-abundance protein concentrates were subsequently subjected to an enzymatic digestion step.

Glycodepletion

Prior to any pre-treatment, defined quantities of PSAQ™ protein (see table 2) were added to 18 μl of serum or plasma previously sampled from a subject, whether they were a carrier of acute liver injury or a healthy donor so as to be able to quantify the presence of this protein in the subject's serum. The serum-PSAQ™ solution was then left incubated for 1 hour at 4° C. under gentle stirring.

The sample of serum or plasma previously taken from a patient, whether they were a carrier of acute liver injury or a healthy donor, and supplemented with PSAQ standards, was mixed with 11 µl of a 0.1 M sodium meta-periodate solution in order to oxidise the glycoproteins and convert the cis-diol groups of the sugars into aldehydes. The sample including glycoproteins bearing aldehyde groups and non-glycosylated proteins was introduced on an affinity column of the Life Technologies GlycoLink kit according to the manufacturer's instructions. The affinity column used comprises an UltraLink resin functionalised with hydrazide. The resin functionalised in this way will be suitable for extracting the glycoproteins present in the serum by creating stable bonds between the hydrazide of the resin and the aldehydes of the previously modified glycoproteins. The non-glycosylated proteins were subsequently eluted by centrifugation in the presence of 400 µl of urea at a concentration of 8M. The sample was concentrated up to 50 µl on an ultrafiltration device having an exclusion limit of 3000 Da and then was subjected to digestion.

Calibration Curves

In order to be able to quantify the presence of a target protein in a human serum sample, calibration curves were produced after the biological sample pre-treatment steps (FIGS. 2 and 3). For each curve, 5 calibration points were produced by adding an increasing quantity of non-labelled protein and a constant quantity of PSAQ™ standard protein to the plasma samples. The quantity of non-labelled proteins added was adjusted so as to cover all the most extreme serum/plasma concentrations in the disease studied. Blanks containing only endogenous biomarkers were also produced. For the 2 lowest calibration points, 4 replicas were produced. These calibration curves made it possible to assess the analytical performances of the assay (linearity of response, precision, accuracy, sensitivity). As demonstrated in FIGS. 2 and 3, the target protein assay has a high performance and may be applied to conventional sample analysis.

Proteolysis

A digestion solution was prepared using a mixture of EndolysC and trypsin (Promega, Charbonnières-les-Bains, France) at a protein/enzyme ratio of 1:30 by mass in a solution of 4 M urea and of $NH_4HCO_3$ at 50 mM at 37° C.

After 3 hours of incubation, the samples were diluted four times and incubated overnight at 37° C. Digestion was stopped by adding formic acid (0.1% in final concentration). The samples were purified on a SinColumns macro C18 column (Harvard Apparatus, Les Ulis, France) and dried by vacuum centrifugation. The pellets were resolubilised in 15 µl of a solution containing 2% by volume of acetonitrile, formic acid at 0.1% by volume.

6 µl of this solution was injected onto the liquid chromatography-mass spectrometer system in SRM mode (LC-SRM).

LC-SRM Analysis

The LC-SRM analyses were carried out on a 6500 QTrap type mass spectrometer (AB Sciex, Les Ulis, France) equipped with a TurboV source and controlled by Analyst software (version 1.6.1, AB Sciex) in a range from 400 to 1000 m/z. The instrument was coupled with an Ultima 3000 LC chromatography system (Thermo Scientific, Courtaboeuf, France). The chromatography of the samples was carried out using a system combining 2 solvents, solvent A (2% acetonitrile and formic acid at 0.1%) and solvent B (80% acetonitrile, formic acid 0.1%). The proteolytic peptides were concentrated on a 1×15 mm C18 PepMap pre-column (Thermo Scientific) and then were separated on a Kinetex XB-C18 column (2.1×100 mm, 1.7 µm, 100 Å; Phenomenex, Le Pecq, France) in gradient mode. As such, the graduation elution was carried out so as to modify the concentration of the initial solution from B at 3% to 35% in 30 minutes, then from 35% to 90% in 10 minutes, at a flow rate of 50 µl/min.

The LC-SRM data analysis and identification of the peaks of each peptide was subsequently carried out using Skyline software. In addition to the assessment of the peptide signal (composite signal originating from multiple transitions), all the transitions were inspected individually and excluded if they were deemed unsuitable for quantification (poor signal-to-noise ratio, obvious interferences). The ratios of the peak areas relative to the labelled and non-labelled peptides were computed for each SRM transition. These ratios were subsequently used to determine the corresponding mean ratio, and finally the mean ratio of the abundance of the target protein was computed on the basis of the ratios obtained for the various signature peptides. The concentration of the biomarkers was subsequently computed on the basis of the mean ratio obtained for each of the proteins. The lower limit of detection (LLD) was determined according to the calibration curve method and the lower limit of quantification (LLQ) is defined as being equal to 3 times the LLD. For each patient, the concentration of the target biomarkers was determined at different times t. FIGS. 4 and 5 show the longitudinal monitoring of the serum concentrations of the different biomarkers in patients suffering from ALI or ALF and for whom the aetiology is either paracetamol (FIG. 4) or another cause (FIG. 5). (see FIGS. 4 and 5). This monitoring is analysed in parallel with the standard clinico-biological parameters (transaminase levels, clotting parameters). In patients with paracetamol-induced ALI/ALF (FIG. 4), the serum concentrations of the biomarkers increase with the progression of the hepatic disorder, in particular the biomarkers ADH1B, ADH1B and ADH1A, BHMT1, BHMT1 and BHMT2, and ADH4 which reach very elevated circulatory concentrations. The concentrations fall while the clinical status and the conventional clinico-biological parameters improve. For patients suffering from ALI/ALF of varied aetiologies, these modifications may also be observed but the serum levels detected are globally lower. FIG. 7 relates to patients suffering from NASH. In these patients, the assay of the target biomarkers in the acute phase of the disease exhibits significantly higher serum concentrations of BHMT1, ADH1A and ADH1B than in healthy donors. This observation demonstrates that the target biomarkers are of interest in NASH diagnosis.

The invention claimed is:

1. A method of determining the presence and/or concentration of a protein ADH1B (SEQ ID NO: 2) or a combination of proteins ADH1A (SEQ ID NO: 1) and ADH1B (SEQ ID NO: 2) in a subject, comprising:
   obtaining a blood sample from the subject; and
   determining the presence and/or concentration of said protein(s) in the sample using one or more signature peptides comprising a signature peptide of SEQ ID NO: 17 for the protein ADH1B and a signature peptide of SEQ ID NO: 15 or SEQ ID NO: 16 for the combination of proteins ADH1A and ADH1B.

2. The method according to claim 1, which further comprises determining the presence and/or concentration of one or more additional proteins selected from the group consisting of: ADH4 (SEQ ID NO: 3, SEQ ID NO: 4), BHMT1 (SEQ ID NO: 5), BHMT2 (SEQ ID NO: 6, SEQ ID NO: 7), ARG1 (SEQ ID NO: 8, SEQ ID NO: 9, SEQ ID NO: 10), FABP1 (SEQ ID NO: 11), GSTA1 (SEQ ID NO: 12) and ALT1 (SEQ ID NO: 13).

3. The method according to claim 1, which further comprises determining the presence and/or concentration of one or more additional proteins selected from the group consisting of: ADH4 (SEQ ID NO: 3, SEQ ID NO: 4), BHMT1 (SEQ ID NO: 5) and BHMT2 (SEQ ID NO: 6, SEQ ID NO: 7).

4. The method according to claim 1, which comprises determining the presence and/or concentration of the protein ADH1B or the combination of the proteins ADH1B and ADH1A; the protein ADH4 (SEQ ID NO: 3, SEQ ID NO: 4); and the protein BHMT1 (SEQ ID NO: 5) and/or BHMT2 (SEQ ID NO: 6, SEQ ID NO: 7).

5. The method according to claim 2, which comprises the determination of the protein BHMT1 (SEQ ID NO: 5), the protein BHMT2 (SEQ ID NO: 6 and SEQ ID NO: 7) or both said proteins.

6. The method according to claim 1, which further comprises determining the presence and/or concentration of the protein CK18.

7. The method according to claim 1, wherein said signature peptide is generated from said protein by an enzymatic digestion process.

8. The method according to claim 2, wherein the presence and/or concentration of said additional proteins is determined using one or more signature peptides selected from the group consisting of:
   SEQ ID NO: 20, SEQ ID NO: 18 and SEQ ID NO: 19 for the protein ADH4;
   SEQ ID NO: 25, SEQ ID NO: 24 and SEQ ID NO: 26 for the protein ARG1;
   SEQ ID NO: 21, SEQ ID NO: 23 and SEQ ID NO: 22 for the protein BHMT;
   SEQ ID NO: 21 for the protein BHMT1;
   SEQ ID NO: 23 and SEQ ID NO: 22 for the combination of proteins BHMT1 and BHMT2,
   SEQ ID NO: 27, SEQ ID NO: 28 and SEQ ID NO: 29 for the protein FABP1;
   SEQ ID NO: 30 for the protein GSTA1; and
   SEQ ID NO: 34, SEQ ID NO: 35 and SEQ ID NO: 36 for the ALT1 protein.

9. The method according to claim 2, wherein the presence and/or concentration of ALT1 protein is determined using the signature peptide SEQ ID NO: 34 or SEQ ID NO: 35.

10. The method according to claim 1, wherein the subject has or is suspected of having a liver disorder chosen from acute liver injury, hepatic steatosis and steatohepatitis.

11. The method according to claim 1, wherein the subject has or is suspected of having a non-alcoholic steatohepatitis.

12. The method according to claim 1, wherein the subject has been previously administered potentially toxic molecules.

13. A method of determining the presence and/or concentration of a protein ADH1B (SEQ ID NO: 2) or a combination of proteins ADH1A (SEQ ID NO: 1) and ADH1B (SEQ ID NO: 2) in a subject, using at least one signature peptide characteristic of the selected protein(s), comprising the steps:
   (a) obtaining a blood sample taken from a subject at the time $t_0$,
   (b) adding a known quantity of an isotopically labelled protein homologous to the selected protein(s), in the blood sample obtained in step a),
   (c) treating the sample to extract at least a portion of the abundant proteins or at least a portion of the glycoproteins,
   (d) treating the sample after extracting at least a portion of the abundant proteins or glycoproteins to generate proteolytic peptides including the signature peptides of said selected protein(s),
   (e) quantitative assay by mass spectrometry of at least one signature peptide generated from the selected protein (s),
   (f) determining a ratio of the abundance of the isotopically labelled signature peptide, from the standard, added in step b), to the abundance of the non-labelled signature peptide from the blood sample, and
   (g) computing the concentration of said selected protein (s) in the sample based on the ratio obtained in step f) and on the known quantity of said isotopically labelled protein added in step b).

14. The method according to claim 13, wherein step (c) is performed by glycodepletion.

15. The method according to claim 13, wherein the method is performed at a time $t_0$ and at a time $t_1$ greater than $t_0$, and comprises after step (g) the comparison of the concentration of the selected protein(s) in the sample between $t_1$ and $t_0$.

16. The method according to claim 13, wherein step (d) is performed by enzymatic digestion using trypsin or a mixture of EndolysC and trypsin.

17. The method according to claim 13, wherein the subject has or is suspected of having a liver disorder chosen from acute liver injury, hepatic steatosis and steatohepatitis.

18. The method according to claim 13, wherein the subject has or is suspected of having a non-liver steatohepatitis.

19. The method according to claim 13, wherein the subject has been previously administered potentially toxic molecules.

20. The method according to claim 1, wherein the blood sample is selected from the group consisting of blood, plasma and serum.

21. The method according to claim 13, wherein the blood sample is selected from the group consisting of blood, plasma and serum.

* * * * *